United States Patent
Lazarewicz et al.

(10) Patent No.: US 9,420,960 B2
(45) Date of Patent: Aug. 23, 2016

(54) STEREO DATA REPRESENTATION OF BIOMEDICAL SIGNALS ALONG A LEAD

(75) Inventors: Maciej T. Lazarewicz, Maple Grove, MN (US); Gabriela C. Molnar, Fridley, MN (US); Jeffrey R. Dixon, Andover, MN (US); Deborah A. McConnell, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 1059 days.

(21) Appl. No.: 13/090,658

(22) Filed: Apr. 20, 2011

(65) Prior Publication Data
US 2012/0101552 A1     Apr. 26, 2012

Related U.S. Application Data

(60) Provisional application No. 61/405,554, filed on Oct. 21, 2010.

(51) Int. Cl.
| | | |
|---|---|---|
| A61N 1/36 | (2006.01) | |
| A61B 5/0476 | (2006.01) | |
| A61B 5/0484 | (2006.01) | |

(Continued)

(52) U.S. Cl.
CPC ............. *A61B 5/0476* (2013.01); *A61B 5/0484* (2013.01); *A61B 5/743* (2013.01); *A61B 5/686* (2013.01); *A61B 5/6868* (2013.01); *A61N 1/36064* (2013.01); *A61N 1/36067* (2013.01);

(Continued)

(58) Field of Classification Search
CPC  A61N 1/372; A61N 1/37211; A61N 1/37247
USPC ................................................... 607/32, 62
See application file for complete search history.

(56) References Cited

U.S. PATENT DOCUMENTS

| | | |
|---|---|---|
| 4,135,089 A | 1/1979 | McIntyre |
| 4,417,590 A | 11/1983 | Smith et al. |

(Continued)

FOREIGN PATENT DOCUMENTS

| | | |
|---|---|---|
| WO | WO95/10979 | 4/1995 |
| WO | WO2011/128823 | 10/2011 |

OTHER PUBLICATIONS

Lehmann et al., "Reference-Free Identification of Components of Checkerboard-Evoked Multichannel Potential Fields," Electroencephalography and Clinical Neurophysiology, 1980, 48: 609-621.

(Continued)

*Primary Examiner* — Amanda Patton
(74) *Attorney, Agent, or Firm* — Shumaker & Sieffert, P.A.

(57) ABSTRACT

Various embodiments concern sensing bioelectrical signals using electrodes along a lead, the electrodes having a spatial configuration along the lead, generating signal data sets, one signal data set being generated for each bioelectrical signal, and graphically representing the electrodes and data representations of the signal data sets on a display. In various embodiments, each data representation indicates a parameter of a respective one of the data sets, the electrodes are graphically represented on the display in a spatial configuration representative of the spatial configuration of the electrodes along the lead, and each data representation is graphically represented on the display in spatial association with at least one electrode through which the bioelectrical signal on which the signal data set is based was sensed. The parameter can be indicative of the relative presence of a biomarker in the bioelectrical signals.

29 Claims, 11 Drawing Sheets

(51) Int. Cl.
*A61B 5/00* (2006.01)
*A61N 1/372* (2006.01)

(52) U.S. Cl.
CPC ......... *A61N 1/36082* (2013.01); *A61N 1/37247* (2013.01)

(56) References Cited

U.S. PATENT DOCUMENTS

| | | | |
|---|---|---|---|
| 5,820,568 | A | 10/1998 | Willis |
| 6,115,626 | A | 9/2000 | Whayne |
| 6,230,049 | B1 | 5/2001 | Fischell et al. |
| 6,909,917 | B2 * | 6/2005 | Woods et al. .................. 607/46 |
| 7,305,268 | B2 * | 12/2007 | Gliner et al. .................. 607/45 |
| 7,346,382 | B2 | 3/2008 | McIntyre et al. |
| 7,623,918 | B2 | 11/2009 | Goetz |
| 7,657,319 | B2 | 2/2010 | Goetz et al. |
| 7,680,526 | B2 | 3/2010 | McIntyre et al. |
| 7,715,673 | B2 | 5/2010 | Fu et al. |
| 7,729,773 | B2 | 6/2010 | Sloan |
| 7,744,607 | B2 | 6/2010 | Wascher |
| 7,822,483 | B2 | 10/2010 | Stone et al. |
| 7,826,902 | B2 | 11/2010 | Stone et al. |
| 7,848,802 | B2 | 12/2010 | Goetz et al. |
| 7,860,548 | B2 | 12/2010 | McIntyre et al. |
| 7,904,134 | B2 | 3/2011 | McIntyre et al. |
| 2006/0015153 | A1 * | 1/2006 | Gliner et al. .................. 607/45 |
| 2006/0111644 | A1 | 5/2006 | Guttag et al. |
| 2007/0083193 | A1 * | 4/2007 | Werneth et al. .................. 606/41 |
| 2007/0129774 | A1 * | 6/2007 | Bourget et al. .................. 607/62 |
| 2007/0203540 | A1 | 8/2007 | Goetz et al. |
| 2007/0288064 | A1 | 12/2007 | Butson et al. |
| 2009/0118635 | A1 | 5/2009 | Lujan |
| 2009/0192556 | A1 | 7/2009 | Wu et al. |
| 2009/0208073 | A1 | 8/2009 | McIntyre et al. |
| 2009/0287271 | A1 | 11/2009 | Blum et al. |
| 2009/0287272 | A1 | 11/2009 | Kokones et al. |
| 2010/0063411 | A1 | 3/2010 | Donoghue et al. |
| 2010/0100153 | A1 | 4/2010 | Carlson et al. |
| 2010/0152817 | A1 * | 6/2010 | Gillbe .................. 607/72 |
| 2010/0305665 | A1 * | 12/2010 | Miesel et al. .................. 607/62 |
| 2011/0046692 | A1 * | 2/2011 | Kalgren et al. .................. 607/32 |
| 2011/0066407 | A1 | 3/2011 | Butson et al. |
| 2011/0319962 | A1 | 12/2011 | Wu et al. |

OTHER PUBLICATIONS

PCT/US2011/056666: Search Report and Written Opinion dated Feb. 24, 2012.

* cited by examiner

1200

1300

STEREO DATA REPRESENTATION OF BIOMEDICAL SIGNALS ALONG A LEAD

This application claims the benefit of U.S. Provisional Patent Application No. 61/405,544, filed Oct. 21, 2010, the entire content of which is incorporated herein by reference.

TECHNICAL FIELD

The disclosure relates to medical devices, and, more particularly, to medical device programming and data presentation.

BACKGROUND

Implantable medical devices, such as electrical stimulators, may be used in different therapeutic applications. In some therapy systems, an implantable electrical stimulator delivers electrical therapy to a target tissue site within a patient with the aid of one or more medical leads that include electrodes. During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may include the configuration of electrodes used to deliver the electrical stimulation therapy.

SUMMARY

In general, the disclosure is directed to collecting data from a plurality of different electrode combinations, processing the data, and presenting the data simultaneously for each of the plurality of electrode combinations.

Various embodiments of the present disclosure concern stereo data representation along a sensing lead by sensing a plurality of bioelectrical signals using a plurality of electrodes along a lead, the plurality of electrodes having a spatial configuration along the lead; generating a plurality of signal data sets, one signal data set being generated for each bioelectrical signal of the plurality of bioelectrical signals; and graphically representing the electrodes and data representations of the signal data sets on a display, wherein the electrodes are graphically represented on the display in a spatial configuration representative of the spatial configuration of the plurality of electrodes along the lead and each data representation of each signal data set is graphically represented on the display in spatial association with the electrode through which the bioelectrical signal on which the signal data set is based was sensed.

Such embodiments may further include that each of the plurality of bioelectrical signals is sensed using a different electrode combination of the plurality of electrodes; and that each signal data set on the display is graphically represented in spatial association with the electrode combination with which the bioelectrical signal on which the signal data set is based was sensed.

Various embodiments may include that generating the plurality of signal data sets comprises generating a plurality of traces, each trace of the plurality generated from a respective one of the plurality of bioelectrical signals; and that graphically representing the signal data sets comprises graphically representing the traces. Various embodiments may include that generating the plurality of signal data sets comprises generating a plurality of indicators, each indicator of the plurality indicative of the strength of an electrode of the plurality in sensing a particular signal component. Various embodiments may include that the particular signal component is beta band power content. Various embodiments may include that the plurality of indicators comprises a plurality of graphs.

Various embodiments may further include displaying representations of the plurality of electrodes as having different coloring between the electrodes to indicate relative strength in sensing a particular signal component. Various embodiments may further include comparing the data sets of the plurality of data sets to each other, wherein graphically representing the signal data sets comprises only displaying a number of those data sets that are associated with superior sensing of a particular signal component relative to others of the signal data sets based on the comparison, wherein the number is at least two. Various embodiments may further include graphically representing the electrodes on the display further comprises graphically representing a body of the lead on the display.

Various embodiments may further include that graphically representing the electrodes and the signal data sets on the display further comprises graphically representing an anatomical brain model on the display and graphically representing the electrodes in spatial association with the brain in a manner calculated to represent the spatial association of the lead in a human brain. Various embodiments may further include graphically representing a tissue activation profile proximate one or more of the electrodes on the display, the tissue activation profile representative of brain tissue that would be activated by electrical stimulated delivered using the electrode proximate the tissue activation profile.

Various embodiments may further include that each signal data set is graphically represented on the display in proximate spatial association with the electrode on which the signal data set is based such that the closest signal data on the display to any electrode is the signal data that is based on the bioelectrical signal sensed using the electrode.

Various embodiments may include that each signal data set is graphically represented on the display in proximate spatial association with the electrode combination on which the signal data set is based such that the closest signal data on the display to any electrode combination is the signal data that is based on the bioelectrical signal sensed using the electrode combination. In some embodiments, the lead is coupled with an implantable medical device. Various embodiments may include that generating the plurality of signal data sets comprises evaluating the plurality of bioelectrical signals to identify one or more biomarkers; and that the signal data sets are indicative of the presence of the one or more biomarkers.

Some embodiments may include a system comprising: a lead having a plurality of electrodes; a display; and control circuitry comprising a processor and memory having stored program instructions executable by the processor, the control circuitry configured to perform any of the above described steps using the lead and the display, or any other steps referenced herein. Some embodiments may include a computer-readable medium comprising instructions that cause a programmable processor to perform any of the above described steps, or any other steps referenced herein. Some embodiments may include a system having means for performing any of the above described steps, or any other steps referenced herein.

Various embodiments concern a system comprising a lead having a plurality of electrodes, the plurality of electrodes having a spatial configuration along the lead, a display, and control circuitry comprising a processor and memory storing program instructions executable by the processor, the control circuitry configured to sense a plurality of bioelectrical signals using the plurality of electrodes, generate a plurality of signal data sets, one signal data set being generated for each bioelectrical signal of the plurality of bioelectrical signals, and graphically represent the electrodes and a plurality of data representations of the signal data sets on the display, wherein the control circuitry is configured to graphically represent the electrodes and the plurality of data representations such that each data representation of the plurality indicates a parameter of a respective one of the plurality of data sets, the electrodes are graphically represented on the display in a spatial configuration representative of the spatial configuration of the plurality of electrodes of the lead, and each data representation is graphically represented on the display in spatial association with at least one electrode through which the bioelectrical signal on which the signal data set is based was sensed.

The generation of the signal data sets by the control circuitry may determine the relative presence of a biomarker in each of the plurality of bioelectrical signals, and wherein the parameter is indicative of the relative presence of the biomarker. In such cases, the biomarker may comprise one or both of beta band power content and gamma band power content. In such embodiments, the parameter may be indicated for each data representation by one or more of color, number, and line pattern, and wherein the color, number, and line pattern are each variable based on the relative presence of the biomarker.

In various system embodiments, the control circuitry may be configured to sense each of the plurality of bioelectrical signals using a different electrode combination of the plurality of electrodes, and graphically represent each data representation on the display in spatial association with the electrode combination with which the bioelectrical signal on which the parameter of the data representation is based was sensed.

In various system embodiments, the control circuitry may be configured to generate a plurality of traces as a part of generating the plurality of signal data sets, each trace of the plurality generated from a respective one of the plurality bioelectrical signals, and graphically represent the traces as part of graphically representing the data representations. In various embodiments, each data representation comprises a line between two of the electrode representations from which the bioelectrical signal on which the data representation is based was sensed.

In various system embodiments, the control circuitry may be configured to deliver electrical stimulation from the plurality of electrodes, sense the plurality of bioelectrical signals timed to collect include invoked response data, and wherein each data representation indicates a first parameter of a stimulation output parameter and a second parameter indicative of the invoked response data.

In various system embodiments, the control circuitry may be configured to compare the data sets of the plurality of data sets to each other, and graphically represent the data representations such that only a number of data representations of those data sets that are associated with greater sensing of a particular signal component relative to others of the signal data sets based on the comparison are displayed, wherein the number is at least two.

In various system embodiments, the control circuitry may be configured to determine a spatial positioning of the lead in a human brain, and graphically represent an anatomical brain model on the display and graphically represent the electrodes in spatial association with the anatomical brain model representing the spatial positioning of the lead in the human brain.

In various system embodiments, the control circuitry may be configured to graphically represent each data representation of each signal data set on the display in proximate spatial association with the electrode on which the signal data set is based such that the closest data representation on the display to any electrode is the data representation that is based on the bioelectrical signal sensed using the electrode.

In various system embodiments, the control circuitry may be configured to graphically represent each data representation on the display in proximate spatial association with the electrode combination on which a associated signal data set is based such that the closest data representation on the display to any electrode combination is the data representation that is based on the bioelectrical signal sensed using the electrode combination.

In various embodiments, the control circuitry is external circuitry, implantable circuitry, or a combination of both external and implantable circuitry distributed between multiple devices. The lead can be coupled to the external control circuitry and/or the implantable control circuitry.

The details of one or more examples of the invention are set forth in the accompanying drawings and the description below. Other features, objects, and advantages of the invention will be apparent from the description and drawings, and from the claims.

DETAILED DESCRIPTION

Leads are used in living beings to sense physiological parameters and/or to deliver therapies, among other things. Numerous different lead designs and configurations are employed to perform these and other functions. While relatively simple leads are still sometimes used, the complexity of leads has grown with the advancement of biomedical techniques and technology. For example, a lead can have eight electrodes, such that at least 36 different combinations exist for bipolar sensing and 8 electrodes for monopolar sensing on the lead alone. A large variety of data processing and presentation techniques further adds to the options available to a clinician for making use of sensed data. The variety and enhanced functionality of leads and other biomedical sensing tools, and well has the expansion of data aggregating options, has added to improved patient care. However, the array of options has complicated matters for a clinician attempting to make effective and efficient use of biomedical devices in diagnosing conditions and treating patients.

The present disclosure includes methods and devices for facilitating the collection, processing, and presentation of sensed data in a manner that is easier for clinicians to understand and use, particularly in a clinical or surgical procedure setting. For example, a lead having eight electrodes may collect data from ten different electrode combinations (without making full use of all electrode combinations). The data for each electrode combination may be stored and processed separately to generate eight different data sets. The processing may chart, plot, convert, summarize, amid/or in some manner refine each data set. The lead can be presented on a display, such as a programmer, each electrode combination of the ten used for sensing also being distinctly indicated on the display. Representations of each data set can then be displayed simultaneously along the indications for each electrode combination with which the data set is associated. The simultaneous display of representations of each data set along the electrode combinations through which each data set was sensed can allow a clinician to quickly understand how different electrode combinations sense a common thing differently. In this way, the clinician can recognize patterns and relationships between different data sets of different electrode combinations, which can facilitate greater understanding of the signals being sensed and selection of preferred electrode combinations for sensing and/or therapy delivery. Furthermore, certain areas of the brain my produce certain biomarkers, such as higher signal content in a particular frequency range. Therefore, recognizing where along a lead sensing a biomarker is strongest via stereo data representation along a lead can facilitate navigating the lead in a brain.

Figure 1:
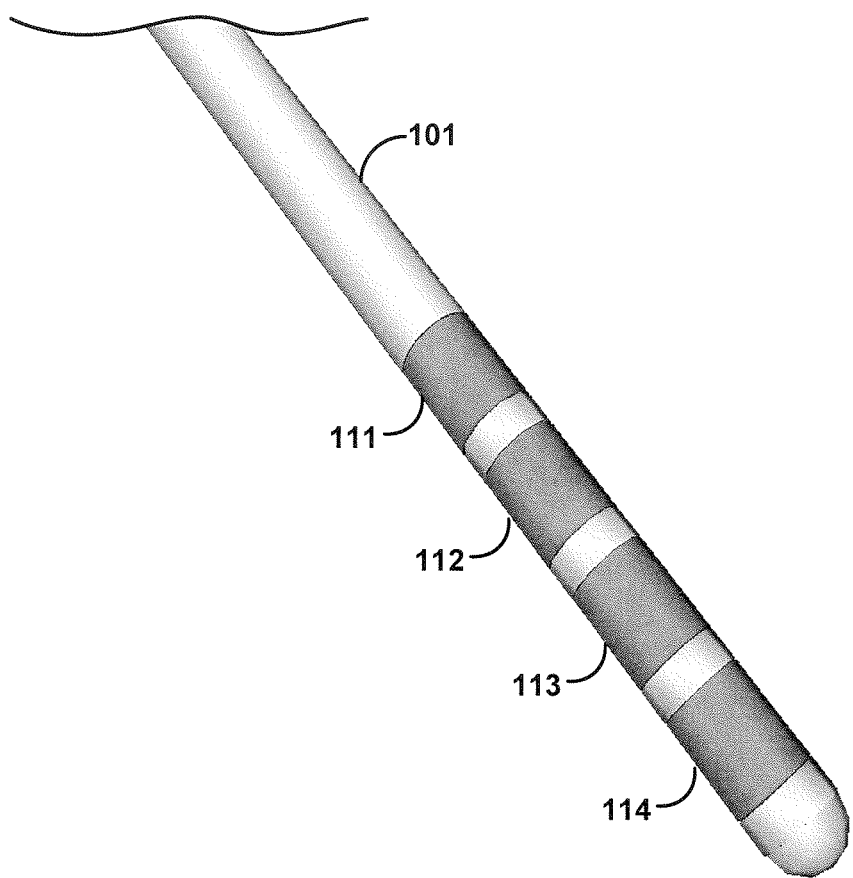
FIG. 1 is a conceptual diagram illustrating a lead useful in deep brain stimulation (DBS).
Figure 2:
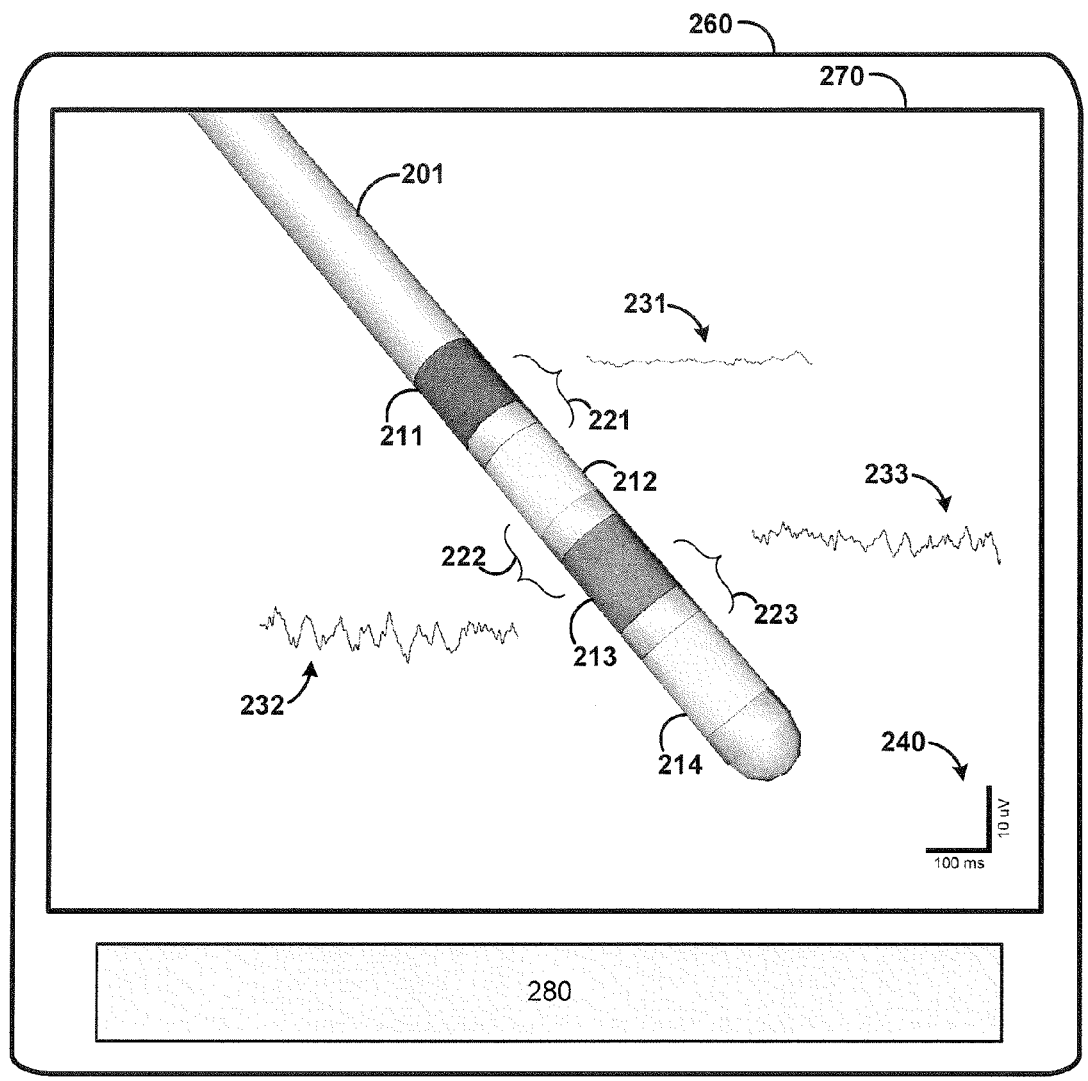
FIG. 2 is a conceptual diagram illustrating a programmer displaying a lead and data representations.

FIGS. 1-2 demonstrate various aspects of stereo data representation. FIG. 1 shows a lead 101. Lead 101 can be, for example, a brain implantable lead configured for sensing bioelectrical signals from within the brain, however not all embodiments of the present disclose are limited to this application. Brain lead applications will generally be discussed in this disclosure because aspects of the present disclosure have particular advantages in brain signal sensing.

Bioelectrical signals sensed within a brain may reflect changes in electrical current produced by the sum of electrical potential differences across brain tissue. Examples of bioelectrical signals include, but are not limited to, local field potentials (LFP), electroencephalogram (EEG), electrocorticogram (ECoG), and/or single unit activity obtained from microelectrode recordings (MER). LFP, however, may include a broader genus of electrical signals within the brain of patient. The particular source of bioelectrical signals sensed from within the brain may normally not be readily apparent because each electrode is surrounded by tissue that could potentially be the source of any given signal. To this end, a certain component of a signal from a particular area of the brain may be targeted for sensing. For example, the gamma frequency band (e.g., about 35 Hz to about 120 Hz) of the subthalamic nucleus may be targeted to investigate the efficacy of a drug in treating Parkinson' Disease (PD) in a patient. However, other sources of signals from surrounding areas can also generate signals, complicating recognition of the targeted signal component. Lead 101 has four electrodes 111-114 spaced along the lead 101. The spatial area covered by the spaced electrodes 111-114 can increase the odds of one electrode being optimally located for sensing the targeted signal component while minimizing repositioning of the lead 101 within the brain.

While increasing the number of electrodes on a lead may aid in sensing a targeted signal with less in vivo repositioning, the number of electrode combinations and signals sensed by the various combinations also increase essentially exponentially. This can create a bewildering number of signals for a clinician to consider for any lead 100 position in the brain. For example, a single lead used in deep brain stimulation (DBS) applications can have eight electrodes, thereby presenting 36 bipolar electrode combination options for sensing. It is noted that mono polar electrodes may also be used and represented as discussed herein, which further adds to the number of sensing options. If a brain is being probed during an implantation procedure for an optimal lead location, then reviewing data from these electrodes efficiently can be particularly important. While lead 101 has fewer then eight electrodes, the four electrodes 111-114 on the lead 101 still present several options for sensing that may need to be considered by a clinician.

FIG. 2 illustrates one example of how data sensed by electrodes 211-214 of the lead 201 can be represented on a display 270 to allow efficient review and electrode selection. Display 270 can be part of a programmer 260 or other external circuitry having a user input. Lead 101 of FIG. 1 is represented on the display as lead representation 201. Likewise, electrodes 111-114 of FIG. 1 are represented on display 270 as electrode representations 211-214, respectively. Select electrode combinations are also indicated by electrode combination identifiers 221-223. For example, the combination of electrodes 211 and 212 is indicated by electrode combination identifier 221, the electrode combination of electrodes 212 and 213 is indicated by electrode combination identifier 222, and the electrode combination of electrodes 213 and 214 is indicated by electrode combination identifier 223.

Sensed data is also shown on the display 270 in association with each electrode combination identifier 221-214. Specifically, data trace 231 is shown associated with combination identifier 221 to indicate that data trace 231 was sensed by electrodes 211 and 212. Data trace 232 is show associated with combination identifier 222 to indicate that data trace 232 was sensed by electrodes 212 and 213. Data trace 233 is show associated with combination identifier 223 to indicate that data trace 233 was sensed by electrodes 213 and 214. Each data trace 231-233 can represent, for example, a certain frequency band of data associated with a target brain area of interest. Each data trace 231-233 is a form of a data representation, as further discussed herein. Display 270 can also show a key 240 having a scale for interpreting the data traces 231-233.

If a clinician is seeking the highest magnitude of signal trace within the frequency band, then clinician can recognize that signal trace 232 represents the highest amplitude of the three signal traces 231-233, and in various cases the preferable electrode combination for sensing and/or therapy delivery. As such, the clinician may use the programmer 260 to program a device to preferentially sense from a particular electrode combination from a plurality of different electrode combinations using the devices and techniques disclosed herein. In particular, the simultaneous display of the traces as data representations of signal data sets allows a one-view comparison of the signal characteristic at interest without changing views on the display 200.

Simultaneous display of representations of multiple data sets along electrode combinations can also allow a clinician to recognize patters and relationships that might not otherwise be apparent. For example, FIG. 2 shows that signal trace 232, corresponding to inner electrode combination electrodes 212 and 213, has the highest signal amplitude while traces 231 and 233, corresponding to outer electrode combinations 221-212 and 213-214, have relatively lower amplitudes. If higher signal amplitude was desirable for a particular application, then the simultaneous display of representations of multiple data sets along electrode combinations shown in FIG. 2 can indicate that in at least the dimension in which the lead 101 is orientated, then an amplitude sweet spot is likely along the lead 101, and not distal or proximal of the electrodes. If signal trace 233 indicated the highest amplitude amongst the signal traces 231-233, then this would indicate that distal movement of the lead 101 in the brain may improve sensing. As such, the stereo representation of multiple data sets along electrode combinations can provide a fuller overview instantaneously to a clinician and drive the targeting of signals of interest.

Also, the stereo representation of multiple data sets along electrode combinations overlaid a brain image can provide a more intuitive understanding of how lead position and orientation affects the electrical environment along the lead. The techniques described herein may help decrease the amount of expertise or experience required to find an efficacious electrode location or combination for sensing and/or stimulation in an efficient manner. Data representations displayed along a lead can include parameters indicating the relative presence of biomarkers associated with specific anatomical structures, such that lead navigation is assisted by stereo display of the lead and data representations on a display, which can be particularly useful when displayed along with an anatomical model.

Although single traces are illustrated in FIG. 2 for select electrode combinations, more traces or other types of data representations can additionally or alternatively be displayed in association with sensing electrodes. For example, data representations in position of traces 231-233 can show square waves or other pattern showing what pulse waveforms were delivered using the associated electrodes. In some embodiments, data representations may show a pulse waveform that was delivered using associated electrodes (e.g., if signal trace 231 was replaced by the pattern of a pulse delivered by electrodes 211 and 212) and show the waveforms or other aspect of sensed elicited responses to the pulse waveforms (e.g., if signal trace 232 represented the evoked response sensed by electrodes 212 and 213). In various embodiments, some data representations will show both the delivered waveform (or other indicator of a parameter of the stimulation) and the evoked response in spatial association with the electrode(s) used for stimulation and sensing of the evoked response. In some other embodiments, some data representations will show the delivered waveforms while other data representations of different electrodes or electrode representations will show the evoke responses. In this way, a data representation can include a parameter of stimulation output, such as pulse amplitude, frequency, duration, shape, and pattern, for each electrode or electrode combination used in delivering stimulation. Such stimulation output parameter may reflect the current configuration that stimulation circuitry is configured to output according to a therapy program. In various embodiments, each data representation may include at least one stimulation output parameter and at least one parameter of a signal data set.

In some data representations, signal data sets taken form two different times corresponding to two different patient states can be displayed in association with the electrode or electrodes through which the signals were sensed. These multiple times may represent different states, such as when the patient is on medication verses off medication, stimulation therapy-on verses stimulation therapy-off, resting verses active, and supine position verses prone position. For example, data representations in position of traces 231-233 can each show a first sensed trace corresponding to a first time when stimulation therapy was delivered and a second sensed trace corresponding to a second time when stimulation therapy was not delivered. As will be appreciated, such representation of data for different patient states along a lead can facilitate understanding by a clinician how the different patient states affect brain electrical activity in different areas of the brain.

Figure 3:
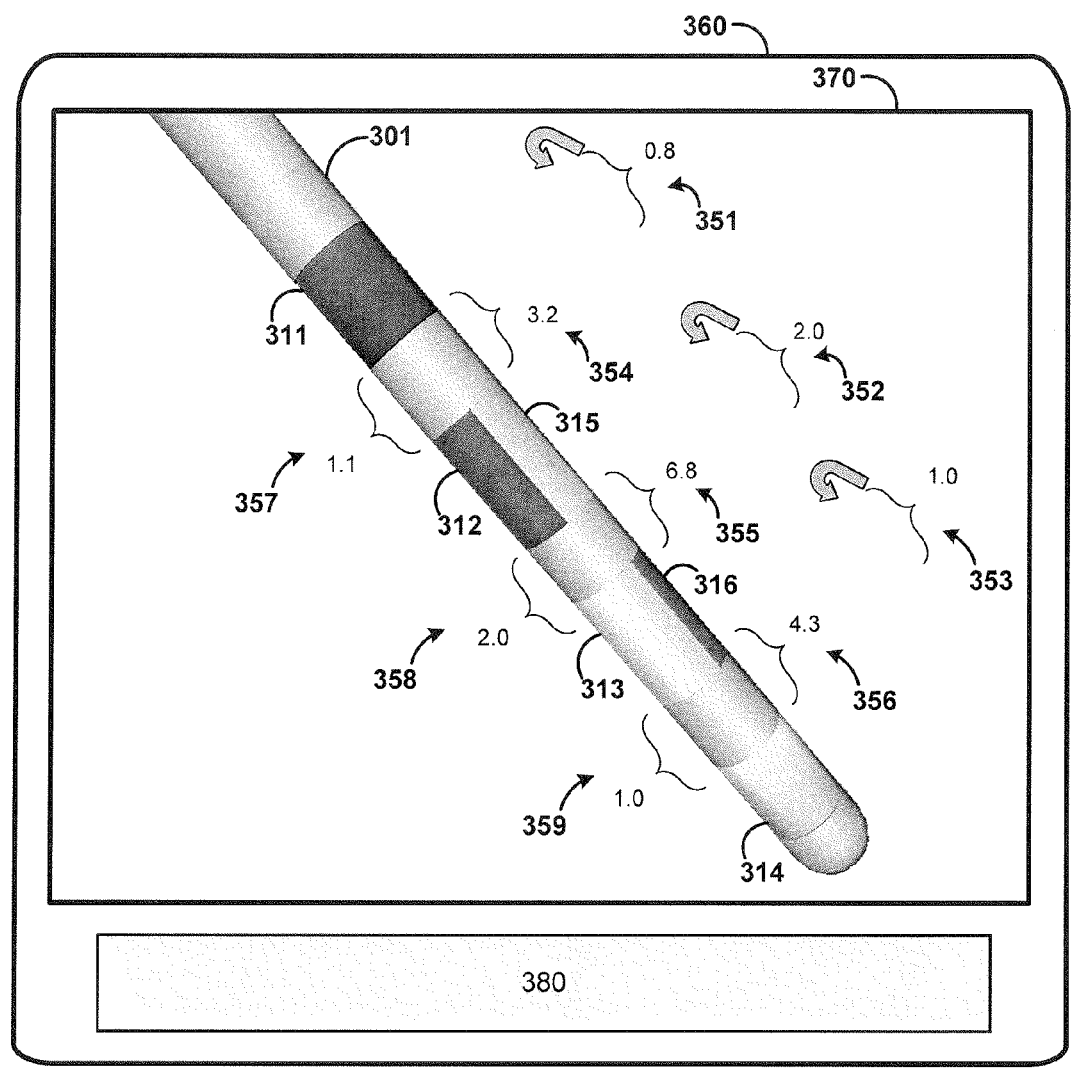
FIG. 3 is a conceptual diagram illustrating a programmer displaying a lead and data representations.

FIG. 3 illustrates an embodiment with a programmer 360 having an input 380 and a display 370. Control circuitry, not illustrated in FIG. 3, can be configured to represent on display 370 a lead 301 having electrodes 311-316. The representation of the lead 301 could be an image, illustration, or some other graphical representation of a lead. Lead 301 is represented as a segmented lead such that not all electrodes are ring electrodes. Electrodes 312 and 315 only cover a circumferential portion of the lead 301, such that two, three, or more electrodes could be located along a common longitudinal length of the lead. In this case, more electrodes are located on the lead 301 than can be shown in the type of representation being shown in FIG. 3. Specifically, one electrode is between electrodes 312 and 315, the electrode sharing the same lengthwise dimension and position as electrodes 312 and 315, but the electrode being on the opposing side of the lead 301. Also, another electrode is between electrodes 313 and 316, the electrode sharing the same length-wise dimension and position as electrodes 313 and 316. In some embodiments, the representation of lead 301 is in some manner transparent and able to show otherwise obscured electrodes. However, in the particular embodiments of FIG. 3, electrodes on the opposite side of the lead 301 are not directly shown.

Sensing aspects of the obscured electrodes may nevertheless be represented. For example, certain electrode pairs are indicated by electrode combinations indicators. Specifically, electrodes 311 and 312 share an indicator showing a value of 1.1, the indicators and values being data representations 351-359 indicating a parameter of the electrode pair. The value represents the relative signal strength in the beta frequency range (12-30 Hz) of a signal sensing using electrodes 311 and 312. In various embodiments, the signal strength is assessed for each of a plurality of electrode combinations relative to the other electrodes of the combination. Electrode combination 311 and 315 are indicated as having a value of 3.2, which indicates that this electrode combination sensed more beta frequency range signal content relative to electrode combination 311 and 312. Other electrode combinations have other indicated beta frequency range content values. Electrode combination 315 and 316 has the highest relative value (6.8) which in some embodiments can indicate that this electrode combination would be the best electrode combination for sensing beta, frequency range content and/or for delivering a stimulation therapy (where greater beta frequency signal content is associated with a greater probability of that electrode combination being able to deliver efficacious stimulation therapy relative to other electrodes associated with less beta frequency signal content).

The relative amount of beta frequency signal content sensed by the obscured electrodes of FIG. 3 is indicated by data representations 351-353 having arrows to indicate reference to electrodes on the reverse side of the lead 301 and with 0.8, 2.0, and 1.0 relative strength based on beta wave sensing. In various embodiments, a value presented with data representations may signify the average, median, peak, lowest, or variance of the signal. For example, the average amplitude of a sensed LFP signal could be presented.

The represented electrodes 311-316 are shown as various colors. Color of electrode representations can be used as a data representation to indicate the presence of a biomarker in signals sensed using these electrodes. For example, electrodes represented in darker color/shading can indicate that less beta frequency range signal content was sensed using these electrodes and lighter colors/shading can indicate that greater beta frequency range signal content was sensed using these electrodes. In the example of FIG. 3, the coloring of electrodes can indicate the relative presence of beta frequency range content sensed in a monopolar configuration while the data representations 351-359 represent the beta frequency range content sensed in a bipolar configuration. In various embodiments, different thresholds can be established, wherein the electrodes or other represented feature are colored/shaded differently depending on which thresholds are crossed. For example, one threshold can represent blue and greater signal content while another threshold can represent yellow and require less signal content to be crossed. In this way, representing electrodes as different colors can quickly convey to a clinician the amount of particular signal content each electrode along a lead is receiving. A key or legend may be provided on the screen to associate a color or range of colors with particular parameter values of a signal data set.

It is noted that brackets are graphically presented in FIG. 3 to group electrode combinations as part of data representations 354-359, the brackets spanning between the and aligned with each electrode combination. In this way, electrode combinations can be graphically associated with one another to indicate a parameter of data sensed from the combination. Other options are available for associating electrode combinations, such as coloring the electrodes of a combination similarly, and other electrodes differently, representing a line connecting each electrode combination, and illustrating a box or other shape surrounding each electrode combination, for example.

Figure 4A:
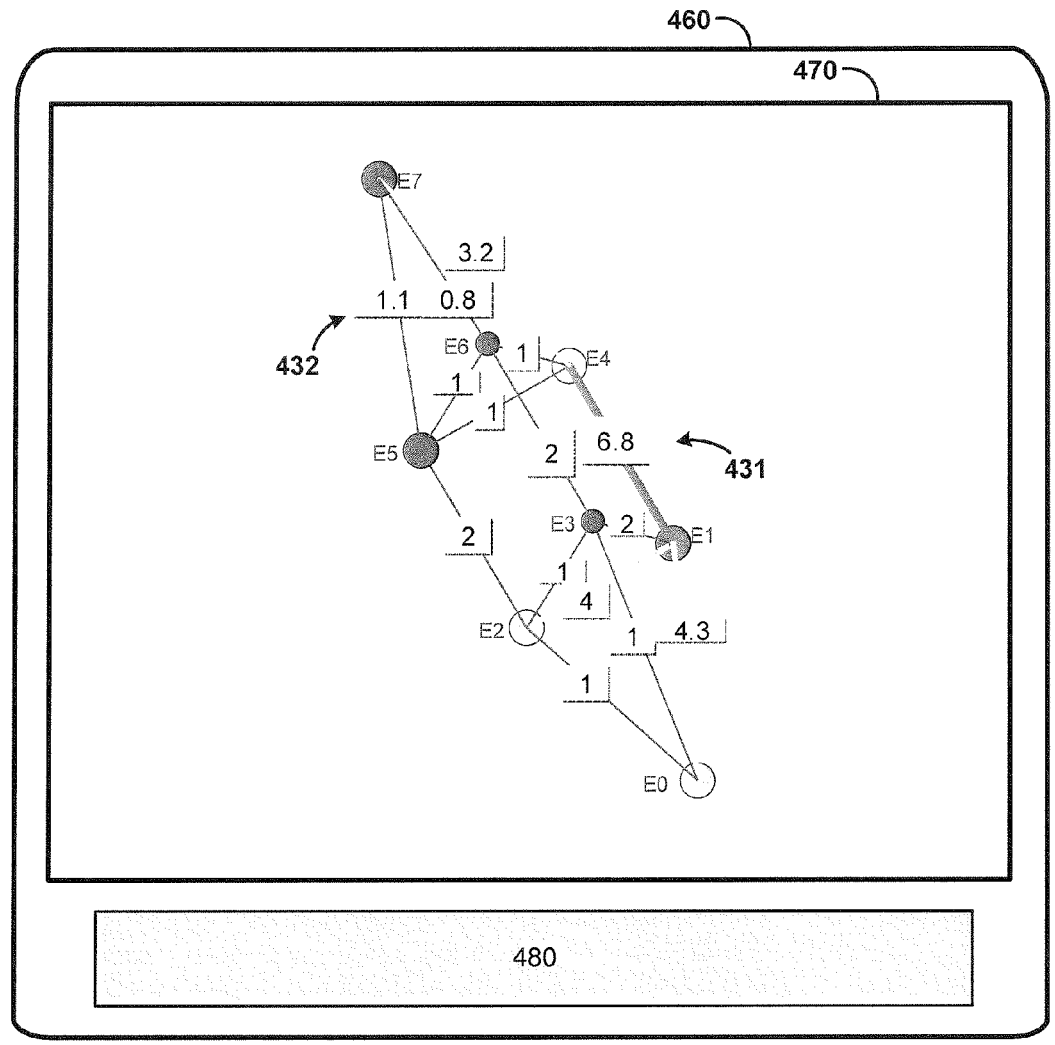
FIGS. 4A-B are conceptual diagrams illustrating a programmer displaying electrode representations and data representations.

FIG. 4A illustrates a programmer 460 having user input 480 and display 470. On display 470 is a three dimensional presentation of stereo data representation. Specifically, a 3D configuration of electrode representations E0-E7 is represented. The electrode representations E0-E7 are displayed in a spatial configuration that represents the spatial configuration of electrodes of a lead, such as the lead 301 represented in FIG. 3. The electrodes E0-E7 are graphically represented on the display 470 in a spatial configuration representative of the spatial configuration of the electrodes along a lead (e.g., a 1×3×3×1 lead 301) because the relative positioning and spacing of the electrodes E0-E7 is similar to that of the actual lead used in sensing (e.g., having the same 1×3×3×1 arrangement of electrodes of the representation of lead 301).

FIG. 4A shows data representations indicating the presence of particular signal content in signals sensed between the electrode combinations. For example, one data representation 431 indicates one or more parameters of a signal data set that is based on a signal sensed between electrode representations E4 and E1 (e.g., a value of 6.8, a darker color/shade, and a thick line). A parameter of the signal may be, for example, the amplitude of the signal or the frequency content of the signal. Each of the value, color/shading, and line thickness of data representation 431 can relate to the same parameter of a signal data set sensed from electrode representations E1-E4, thereby redundantly indicating presence of the same thing (e.g., beta frequency range content). However, in various embodiments, each of these aspects of a data representation, such as data representation 431, can indicate different parameters of a signal data set. For example, line thickness can indicate signal amplitude, color can indicate frequency content, and value can indicate the ratio of content between two frequency ranges determined by control circuitry based on a signaled sensed between an electrode representations E4 and E1. Data representation 432 indicates different coloring, a thinner line, and a lower value (1.1) relative to data representation 432, which can indicate that data representation 432 is better positioned to sense biomarkers of a certain condition or area of the brain.

Data representation values can indicate various parameters, such as total or maximal power in a certain frequency range, signal amplitude, or a ratio between these or other parameters. In some embodiments, a value of a data representation can represent a normalized value. For example, electrode combination E1, E4 having a value of 6.8 can represent stronger sensing of certain signal characteristics relative to minimal sensing of the signal characteristics in electrode combinations E2, E0 and E7, E5, for example. Normalizing can be performed by taking the data from all electrodes and/or electrode combinations and normalizing the data to some scale, such as a ten point scale. Such normalized scales may be easier for a clinician to quickly understand and compare between electrodes than parameter values. Such signal characteristics can be a biomarker to indicate proximity to a targeted area of the brain. As such, electrode combination E1, E4 can be easily recognized to be superior in sensing a certain biomarker relative to electrode combination E2, E5 by a clinician using programmer 460.

The values of data representations can be positioned in spatial association with the electrode representations on which the data representation is based. For example, the value of 6.8 of data representation 431 is spatially associated with electrode representations E1 and E4 because it is between the electrode representations E4 and E1 and also overlaps the line connecting electrode representations E1 and E4. A value can also be proximate the electrode representations or line connecting to the electrode representations to indicate spatial association with the electrodes.

Figure 4B:
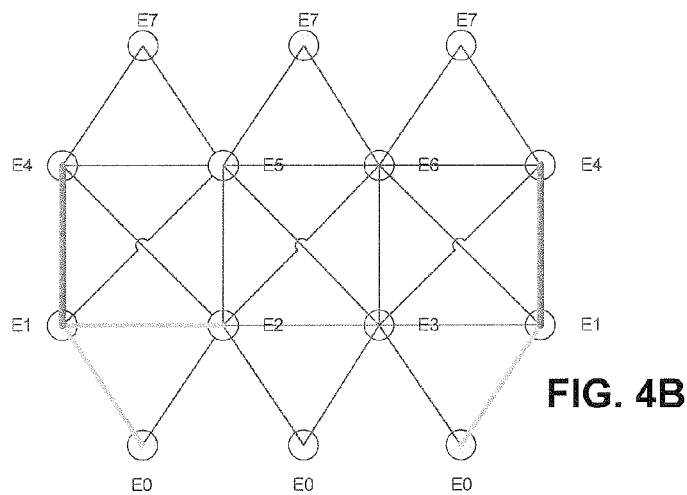

FIG. 4B illustrates an alternative way to represent the electrodes E0-E7 in a two dimensional format. As in other embodiments, color/shading, line thickness and the like can indicate parameters of signal data sets generated from signals sensed for the various combinations of electrode representations E0-E7. It is noted that the two dimensional arrangement represents the various electrode combinations by representing certain electrodes multiple times, such as electrodes representations E0 and E7.

Figure 5:
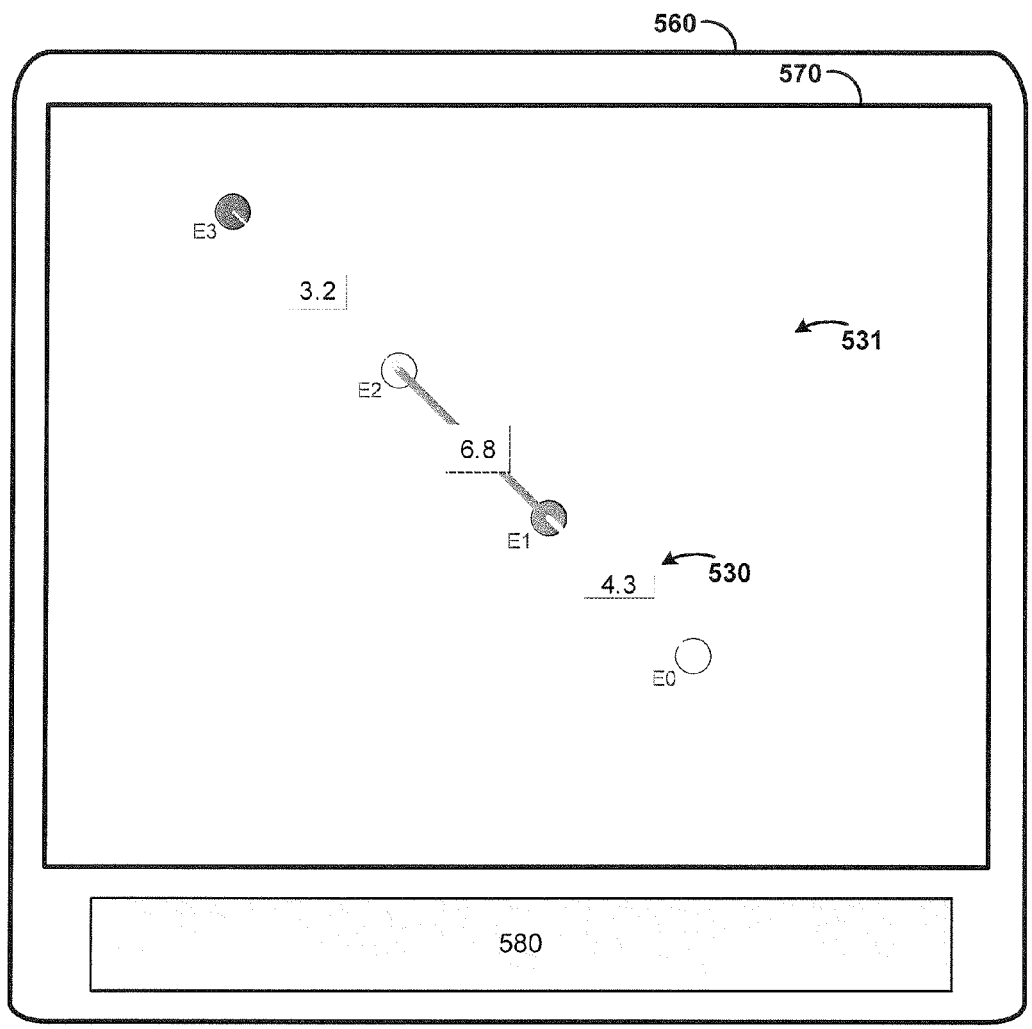
FIG. 5 is a conceptual diagram illustrating a programmer displaying electrode representations and data representations.

FIG. 5 illustrates an embodiment of stereo data representation along a sensing lead. Specifically, programmer 560 having user input 580 and display 570 shows a lead representation 531 having electrode representations E0-E3. The spatial configuration of the electrodes representations E0-E3 can correspond to the lead 101 of FIG. 1 having four electrodes in a 1×1×1×1 configuration. FIG. 5 shows values between various electrode combinations representing the relative signal strength for beta frequency range content signals sensed using the electrodes combinations. For example, the electrode combination E0, E1 has a relative signal strength of 4.3 shown as a data representation over a line connecting the electrodes, which may be preferable for sensing data and/or delivering stimulation relative to electrode combination E2, E3 (having a value of 3.2) but not preferable in view of electrode combination E1, E2 having the highest value of 6.8. The electrode combination E1, E2 can also be colored (e.g., by shading) differently to additionally or alternatively indicate that it is associated with strongest beta frequency range sensing relative to the other electrode combinations. In this way, a plurality of electrode combinations can be colored differently or at least along multiple grades to represent their relative strengths in some function, such as data collection or therapy delivery. In addition to values and colors, lines are shown connecting various electrode combinations as data representations. As discussed herein, line thickness may indicate a parameter of a signal data set, such as an amplitude parameter.

The establishing of relative signal strength values in FIG. 5 can be performed using any technique herein, and can be performed in the same manner as that associated with FIGS. 3, 4, and 6-8, for example.

In some embodiments, the sensing and/or stimulating properties of electrodes of a lead can be graphically represented by coloring of the electrodes on a display as a data representation, such as by shading the electrodes differently. For example, a plurality of electrodes may be used to sense a common signal type and identical signal processing may be performed on the sensed data. An evaluation can then be performed on the data sets to determine the relative strength of each electrode or electrode combination in performing some function. For example, EEG data may be sensed by a plurality of electrode combinations in a lead, transforming the signal (or data from the signal) to the frequency domain from the time domain, and the frequency data evaluated to determine which of the electrodes or electrode combinations is best associated with the sensing beta frequency range signal content, as judged by the power level in the frequency spectrum of the beta frequency range. The electrode or electrode combination that sensed the data set having the highest value may then be colored differently (e.g. having the lightest shading) relative to the other electrodes or electrode combinations associated with lesser sensing quality. The next best electrode or electrode combination as determined using the same technique can then be shaded a darker shade then the electrode or electrode combination associated with highest sensing quality but lighter than the other electrode combinations associated with less sensing quality. In this way, electrode representations can be ranked to provide an intuitive view to a clinician in understanding the sensing quality range along a lead. As discussed herein, the power level or other parameter may also be expressed as a value, line thickness, or other indicator of a data representation. In some cases, electrode representations may be ranked by providing a numerical value on a display in spatial association with the electrode representations. For example, in a lead containing 8 electrodes, the best electrode to be used for therapy delivery may be assigned (e.g., marked with) the number 1, and the electrode least likely to provide efficacious therapy delivery may be assigned the number 8, the ranking based on one of the parameters discussed herein, such as the relative amount of a particular type of signal content sensed by each electrode or electrode combination.

Figure 6:
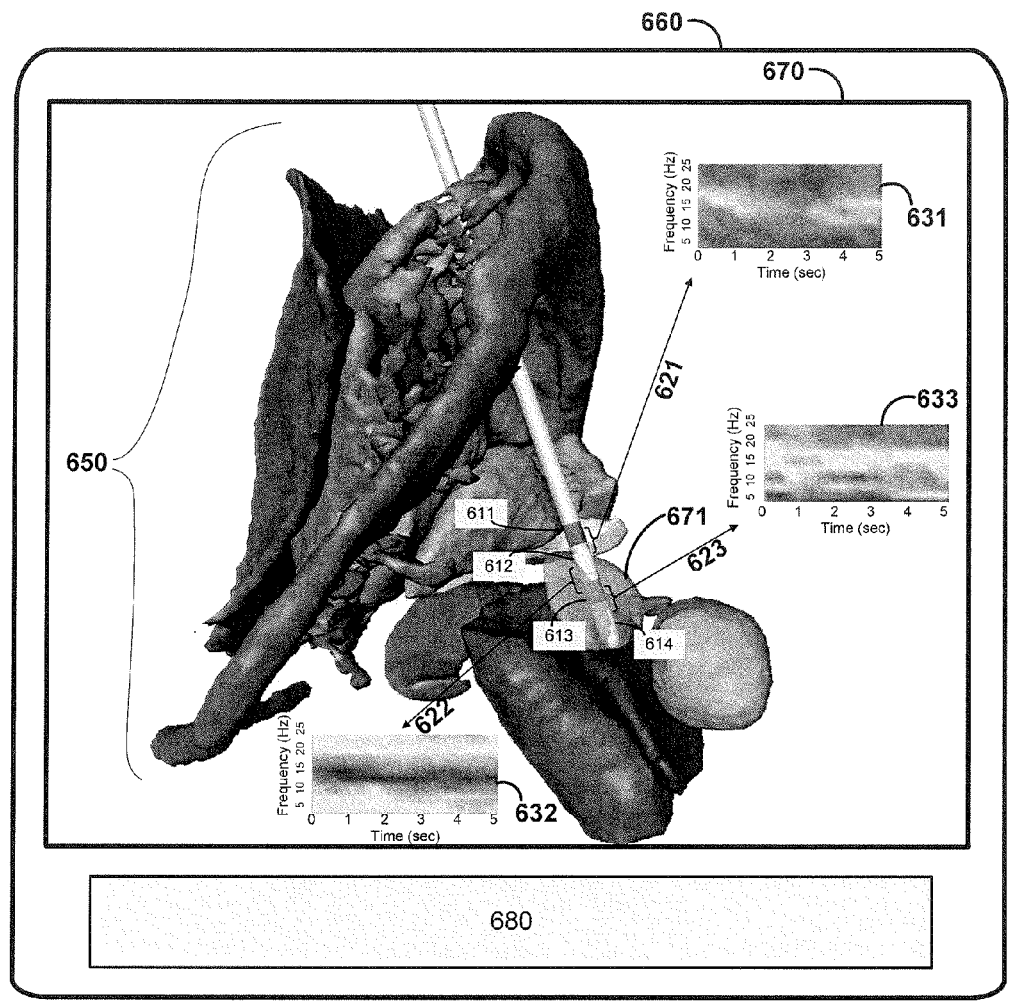
FIG. 6 is a conceptual diagram illustrating a programmer displaying a lead representation, data representations, and an anatomical brain model.

Aspects of the present disclosure can be used with brain or other anatomical models for stereo data representation of biomedical signals. In various embodiments, a physiological model can be generated, stored in memory, and displayed with a representation of a lead and stereo data representation to convey to a clinician how the electrodes along a lead sense differently in the physiological environment modeled. FIG. 6 illustrates a display 600 of a programmer 660 having a user input 680 showing a brain model 650. The brain model may be a predetermined brain model stored in memory (e.g., based on general, non-specific data) or a model generated based on the anatomy of a particular patient. For example, a computing device may be used for mapping patient anatomy data from an imaging modality, such as, but not limited to, CT, MRI, X-Ray, fluoroscopy, and the like. The model can be generated with the aid of modeling software, hardware, or firmware executing on a computing device, such as programmer or a separate dedicated or multifunction computing device.

Lead representation 601 can be located within the brain model 650 using various techniques, including the same techniques used for generating a brain model (e.g., CT, MRI, x-ray, fluoroscopy, and the like). The location of lead representation within the brain model 650 can also be determined using any suitable technique, such as based on a medical image generated using any suitable imaging modality (e.g., fMRI, MRI, CT) based on the stereotactic coordinates used to implant the lead, based on correlations of signals sensed by electrodes with anatomical structures expected to yield those signals (e.g., sensing of known signal signatures of landmarks in the brain, such as template matching), correlations of stimulation effects at electrodes with anatomical structures expected to yield those effects, or based on a clinician-estimated location of a lead.

The data representations 631-633 in FIG. 6 are heat maps showing the frequency content of signals as a function of time sensed by electrode combinations 611-612, 612-613, and 613-614, respectively. Such heat maps are examples of various data representations that can be made in a display using spatial positioning relative to the electrode combination that sensed the data, using electrode combination identifiers 621-623, or in some other manner showing respective data sets simultaneously associated with different electrode combinations along a lead. Electrode combination identifiers 621-623 may include brackets and lines for graphically associating electrode combinations (e.g., electrodes 611 and 612) and data representations (e.g., data representation) based on signal data sensed from the electrode combinations. As with other types of data representations referenced herein, the heat maps can show data that was sensed during a previous period in time, such as a static data set, or can show live real-time representations of what data is being sensed along a lead.

FIG. 6 further shows a therapy field 671 that represents a region of the patient's tissue to which therapy is delivered. In various embodiments, the therapy field 671 can include an electrical stimulation field (also referred to as an electrical field) that is generated when a stimulator delivers electrical stimulation to a brain of patient with a selected subset of electrodes and a therapy program defining stimulation parameters. A therapy field model can indicate the electrical field, activation field, voltage gradient or current density of the electrical field resulting from delivery of stimulation via a specific stimulation electrode combination. Anatomical displays with stereo data representation may also illustrate target volume (e.g., the tissue areas that would be targeted for activation based on models or clinical data) and/or side effect volume (e.g., tissue area that are associated with unintended side effects when stimulated).

In various embodiments, the stereo data representations are static. For example, data representations may represent the signal sensed along a lead at a point in time or over a passed fixed time period. In some embodiments, each representation of data may move a trace might move to show data sensed at different times within a window of time) but nevertheless be limited to data sensed within a certain time window. In various other embodiments, however, the displays of data represent the data sensed (and in some embodiments further processed) in real time for an indefinite period. For example, a trace could show the data live as it is sensed, or as soon as possible after it is sensed accounting for the short amount of time needed to process the data in some manner (e.g., filter and/or plot). Likewise, the values, colors, line thickness and other techniques for indicating a parameter of a signal data set can be changed in real time as the sensing characteristics change, such as when a lead is advanced within the brain. As such, any of the embodiments referenced herein can use either fixed or changing data representations.

In various embodiments, each data representation along a lead on a display represents identical sensing and data processing techniques for each electrode combination. For example, if beta frequency range content is being compared between electrode combinations, then an appropriate technique for sensing, filtering, and representing beta frequency range content (e.g., as with a heat map as disclosed herein) can be performed for each electrode combination. As such, each data representation associated with a different electrode combination can represent data that was sensed, processed, and/or represented in an identical manner as the other representations of the electrode combinations, except for being sensed by different electrodes. In some embodiments, different sensing, processing, and/or representing techniques can be used for different electrode combinations along the same lead. For example, one electrode combination may be associated with sensing, filtering, and data representation optimized for beta frequency range content while another electrode combination is optimized for gamma frequency range content. These different sensing, processing, and/or representing techniques can still be used to generate simultaneous representations of data along a lead corresponding to different electrode combinations.

In some embodiments, while bioelectrical signals may be sensed and processed, data representations may be made for only some of the electrodes or electrode combinations. For example, after a comparison of biomarkers it may be determined that some electrodes or electrode combinations are associated with superior biomarker sensing compared to others, and only those showing superior biomarker sensing (e.g., as evaluated by a threshold comparison or the top three content values) may be shown on the display as data representations. As such, the data representations on a display may represent a limited set of bioelectrical signals that were sensed and not represent data representations for some of the electrode combinations that sensed signal data evaluated to have lesser content. Limiting the number of data representations to those judged best (e.g., automatically by control circuitry of a programmer) may minimize clutter on a display and easily focus the clinician's attention on the most relevant data.

Biomarkers may include one or more signal characteristics. One or more signal characteristics (e.g., time domain characteristic or a frequency domain characteristic) of each of the sensed bioelectrical signals may be compared to each other in some manner and one or more sense electrode combinations may be distinguished based on the comparison, such as displaying values indicating the relative strength of each of a plurality of electrode combinations in sensing some biomarker or performing some other function. An example of a time domain characteristic includes a pattern in the time domain signal over time (e.g., a pattern or number of neuron spikes over time), variability of the time domain signal over time, median, average or peak amplitude of the signal, and the like. An example of a frequency domain characteristic may include power level (or energy level) within a particular frequency band, such as the beta frequency range. The power level may be determined based on, for example, a spectral analysis of a bioelectrical signal. The spectral analysis may indicate the distribution over frequency of the power contained in a signal based on a finite set of data.

In some examples, a biomarker for stereo data representation or ranking electrode combinations can be a time domain pattern substantially correlating to a template stored in memory. In other examples, such a biomarker can be a threshold number of spikes within a particular time frame were observed was sensed. The threshold number of spikes may be indicative of activity within a particular region of brain, and, therefore, sensing a bioelectrical signal with the threshold number of spikes can indicate that sense electrodes are positioned proximate the associated region of brain, which can be displayed using stereo data representation along a sensing lead as discussed herein to show the distribution of spikes sensed along a lead or a parameter of the spikes. In various embodiments, such a biomarker can be a variability of sensed bioelectrical signals for each of a plurality of electrode combinations. For example, a bioelectrical signal having a variability that matches or substantially matches (e.g., is within a threshold percentage, such as about 1% to about 25%) a predetermined variability can be represented for a plurality of electrode combinations along a lead.

In other examples a biomarker for stereo data representation can be based on a mean, median, average or peak amplitude that is greater than or, in some examples, less than, a predetermined threshold value was sensed, or the highest relative band power (or energy) level in a selected frequency band was sensed. This may indicate, for example, that the one or more electrodes with which the bioelectrical signal with the highest relative band power level was sensed is located closest to the target tissue site, which can be a region within brain that produces a bioelectrical signal with the highest relative power level within a selected frequency band. As such, the particular frequency band of interest may be selected based on the patient condition. For example, it is believed that abnormal activity within a beta frequency band (e.g., about 8 Hz to about 30 Hz or about 16 Hz to about 30 Hz) of a bioelectrical signal is indicative of brain activity associated with a movement disorder (e.g., Parkinson's disease), as well as revealing of a target tissue site for therapy delivery to manage the patient condition. Therefore, in some examples, the power level within a beta frequency band of a bioelectrical signal can be used as a biomarker to identify a target tissue site for stimulation therapy to manage a movement disorder.

A target tissue site (targeted for sensing or therapy) can be, for example, the tissue site exhibiting a relatively high beta frequency band energy or the tissue site within brain that exhibits another predetermined frequency band characteristic. The relative beta frequency band power level may be a ratio of the power in a beta band of the sensed signal to the overall power of the sensed signal, and may be used instead of the beta frequency band power in order to normalize the bioelectrical signals sensed by sense electrodes located in different areas of brain.

Power levels and the like can be used as values in data representations for display along electrode representations or otherwise be used as parameters of data representations (e.g., in setting colors, line thickness or other parameter indicators). One example is a beta band power level. The relative beta band power may be a ratio of the power in a beta frequency band of the sensed signal to the overall power of the sensed signal. The relative beta frequency band power may be used instead of the beta frequency band power in order to normalize the bioelectrical signals sensed by sense electrodes located in different regions of a patient's brain. This normalization of sensed brain signals applies to the power level within any selected frequency band. Thus, while "power levels" within a selected frequency band of a sensed brain signal are generally referred to herein, the power level may be a relative power level, which is a ratio of a power level in a selected frequency band of a sensed brain signal to the overall power of the sensed brain signal. The power level in the selected frequency band may be determined using any suitable technique. In some examples, a processor of control circuitry may average the power level of the selected frequency band of a sensed brain signal over a predetermined time period, such as about ten seconds to about two minutes, although other time ranges are also contemplated. In other examples, the selected frequency band power level may be a median power level over a predetermined range of time, such as about ten seconds to about two minutes. The activity within the selected frequency band of a brain signal, as well as other frequency bands of interest, may fluctuate over time. Thus, the power level in the selected frequency band at one instant in time may not provide an accurate and precise indication of the energy of the brain signal in the selected frequency band. Averaging or otherwise monitoring the power level in the selected frequency band over time may help capture a range of power levels, and, therefore, a better indication of the patient's pathological state in the particular brain region sensed by a lead. This analysis may yield a ratio, probability, or confidence level that may be displayed to the user to aid in decision making. In some embodiments, power level may refer to a ratio of power between two frequency bands, such as beta band power to gamma band power.

Figure 7:
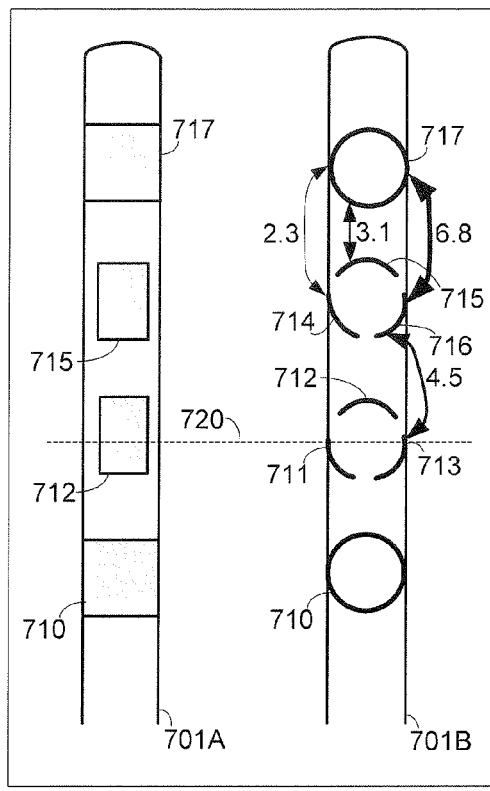
FIG. 7 is a conceptual diagram illustrating display having lead representation and data representations.

FIG. 7 illustrates a display 700 showing a lead representation 701 in A and B configurations. Lead representations 701A and 701B represent a physical lead, such as lead having segmented electrodes, that is, electrodes on a circular lead body that span less than the full circumference of the lead. In some embodiments, three segmented electrodes can be around a common circumference and extend along a common length of the lead. Electrode representations 717 and 710 represent electrode rings that span the full circumference of the lead. Electrode representation 715 shows one of three electrodes along a common longitudinal section of the lead. Likewise, electrode representation 712 shows one of three electrodes along a common longitudinal section of the lead. In each case, the other two electrodes are not visible because the lead representation 701A attempts to graphically represent a physical lead body as if the clinician was looking at the actual lead where the segmented electrodes may be facing away and therefore not visible. As such, it can be difficult to relate multiple parameters associated with multiple electrode combinations in one view. However, in the particular embodiments of FIG. 7, multiple lead representations 701A and 701B are simultaneously shown on display 700 to facilitate an intuitive view of all electrodes combinations and data representations.

Lead representation 701B shows the same lead but with cross sections shown for each electrode set. For example, a thick circle is shown for electrode representation 717 because the electrode is a ring electrode. Electrode representations 715 and 712 represent segmented electrodes and therefore are shown as thick arcs on lead representation 701B. Because the cross sections show the entire lead periphery; electrodes on the opposing side of lead representation 701A are shown as electrode representations 711, 713, 714, and 716. Also, data representations can be shown in spatial association with electrode representations corresponding to the electrodes from which data was sensed. For example, a data representation having a value of 6.8 and a thick arrowed line is shown in spatial association with electrodes 716 and 717. In this embodiment, as in various other embodiments, a higher value and thicker line in a data representation signify that the electrode combination indicated in the data representation is associated with sensing greater signal content of some kind, such as higher proportion of beta frequency band content of a sensed signal relative to other electrodes. Electrode representations 713 and 716 are indicated to have a value of 4.5 and a moderately thick line, which signifies sensing greater signal content of some kind than electrode representation 717 in combination with either electrode representation 714 or 716, which have lesser values (2.3 and 3.1, respectively) and thinner lines.

Alignment indicator 720 shows where the cross section of each electrode or electrode set is taken. Although one alignment indicator 720 is shown, more could be used in different positions. Alignment indicators could be shown in different orientations to show different cross sections, which may be useful for different electrode configurations.

It is noted that the display 700 shows two lead representations 701A and 701B of the same lead. However, one or another number of lead representations may be shown. For example, a display on a programmer may only show one electrode representation at a time, but may switch between lead representations 701A and 701B when an input is made. As such, a user input may allow a clinician to switch through various different views highlighting different aspects of sensing.

Figure 8:
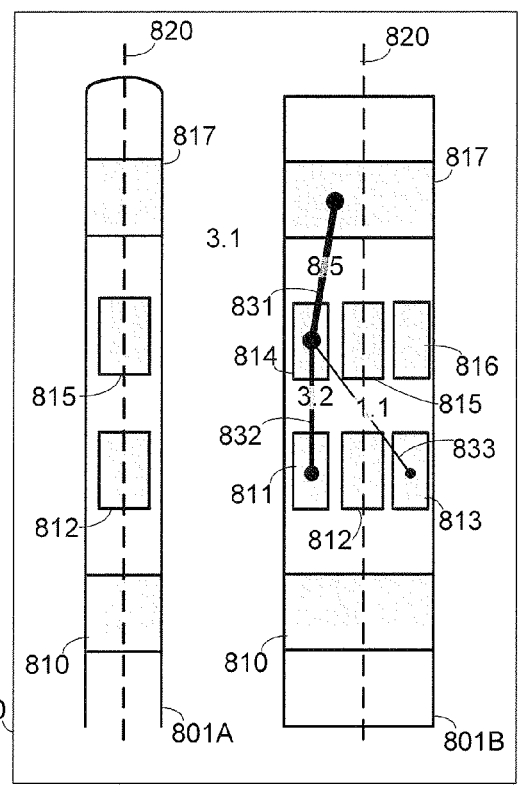
FIG. 8 is a conceptual diagram illustrating display having lead representation and data representations.

FIG. 8 illustrates a display 800 showing a lead representation 801 in A and B configurations. Lead representations 801A and 801B represent a physical lead having 2 ring electrodes and two groups of three segmented electrodes. Electrode representations 810 and 817 represent ring electrodes while electrode representations 812 and 815 represent segmented electrodes. Other segmented electrodes are not represented in lead representation 801A because they would be obscured by the representation of the lead body.

Lead representation 801B is an unrolled version of lead representation 801A. Being in an unrolled configuration, the entire peripheral surface of the lead can be seen for a longitudinal section of the lead. For example, electrode representation 817 is shown as an unrolled electrode spanning the width of lead representation 801B because it wraps around the lead body. Electrode representations 814, 815, and 816 represent a set of three segmented electrodes along a common longitudinal length of the lead. Gaps are shown between the electrode representations 814, 815, and 816 to represent the segmented nature of the segmented electrodes. Electrode representations 811, 812, and 813 also show a group of segmented electrodes unrolled to display all electrodes of the group, some of which would be obscured in a rolled view.

Data representations can be shown in spatial association with electrode representations corresponding to the electrodes from which the data was sensed. For example, data representation 831 having a value of 8.5 and a thick line is shown in spatial association with electrode representations 814 and 817. In this embodiment, as in various other embodiments, a higher value and thicker line in a data representation can signify that the electrode combination indicated in the data representation is associated with greater sensing of some particular signal content. Data representation 832 is indicated to have a value of 3.2 and a moderately thick line, which signifies sensing greater signal content of some kind associated with electrode representations 811 and 814 than the combination of electrode representations 814 and 813 which has a lesser value of 1.1 and a thinner line as indicated by data representation 833.

In FIG. 8, data representations are associated with the particular electrodes of electrode combinations by forming a line spanning between the electrodes. For example, data representation 833 is associated with electrode representations 813 and 814 because data representation 833 includes a line spanning electrode representations 813 and 814. Data representation 833 is likewise positionally associated with electrode representations 813 and 814 by having a value (1.1) between electrode representations 813 and 814, overlapping a line between electrode representations 813 and 814, and being proximate electrode representations 813 and 814.

Alignment indicator 820 shows a common exterior longitudinal axis in both lead representations 801A and 801B. Alignment indicator 820 can be used as a common reference between the two lead representations 801A and 801B to orientate users and allow for point-of-comparisons between the two lead representations 801A and 801B. In both rolled and unrolled configurations, the two lead representations 801A and 801B can be laterally aligned such that the top and bottom of electrode representation 815 of lead representation 801A is laterally aligned with the top and bottom of electrode representation 815 of lead representation 801B.

It is noted that display 800 shows two lead representations 801A and 801B of the same lead. However, one or another number of lead representations may be shown. For example, a display on a programmer may only show one electrode representation at a time, but may switch between rolled lead representation 701A and unrolled lead representation 701B when an input is made. As such, a user input may allow a clinician to switch through various different views highlighting different aspects of sensing, including switching between the various views of FIG. 1-8. In some cases, an input may cause a representation of a lead to rotate, such that different sides of the lead can be viewed. Alternatively, the display perspective can rotate around the lead to likewise allow all side of the lead to be viewed.

Line thickness, color, value, and other identifiers referenced herein for indicating a parameter of a data representation can be used simultaneously in one embodiment. For example, line color and thickness of a data representation may both indicate the relative amount of beta band signal content. The use of redundant indicators of a parameter can be easier for different clinicians with different preferences to easily understand the same presentations. In some embodiments, line thickness, color, value, and other identifiers referenced herein represent different parameters in a single embodiment. For example, in the embodiment of FIG. 8, line thickness may be proportional to the gamma frequency band signal content sensed from an indicated electrode combination while the value of each data representation is proportional to the beta frequency band signal content. While different aspects of data representations may concern similar metrics, such as different frequency bands, in various other embodiments different aspects of the data representations concern different metrics. For example, line thickness may represent the average amplitude of a LFP signal while color or value may signify the amount of signal content in a particular frequency band of a signal. As such, determining and displaying data representations as disclosed herein can facilitate a clinician's quick understanding of the different signal content sensed along a lead body by data representations signifying different biomarkers.

It is noted that the embodiments presented herein generally refer to representing higher signal content, such as determining and representing values that signify the relative amount of beta frequency band content in a signal. Some embodiments may display data representations for only the electrodes or electrode combinations associated with stronger signatures of biomarkers (e.g., only display data representations for the three electrode combinations having the largest signal content in a certain frequency band). However, various embodiments may additionally or alternatively focus on the lowest signal content or a ratio of signal content. For example, a ranking of an electrode combination may rank the lowest amplitude or lowest frequency band content as higher in a ranking than electrode combinations having higher amplitudes or higher amounts of frequency band content. In some embodiments, the value, line color, line thickness or indicator of a parameter of a data representation may signify a ratio of two things, such as ratio of amount of content between two frequency bands (i.e. beta verses gamma bands).

It is noted that the data representations in FIGS. 1-8 include discrete displays of data representations. That is, the data representations are not exclusively grouped together, such as in a table or grouped fields. Rather, the data representations are arranged in the figures to show associations to the electrodes or electrode combinations on which the data representations are based (which may be presented in addition to a table, for example). In some embodiments, the display layout is arranged to position each data representation proximate to the electrode or electrode combination with which it is associated and/or have a line associating a data representation (e.g., a graph) and one or more electrodes for which the data representation is based. Specifically, the data representation indicates a parameter of a signal data set that was generated from a signal sensed using the electrode(s) which the data representation is positionally associated with on a display relative to other electrode(s) on which the data representation is not based. Stereo data representation along a lead in this manner may easily show the direction and/or area from which the strongest signal content was sensed along a lead relative to other directions and areas along the lead.

Figure 9:
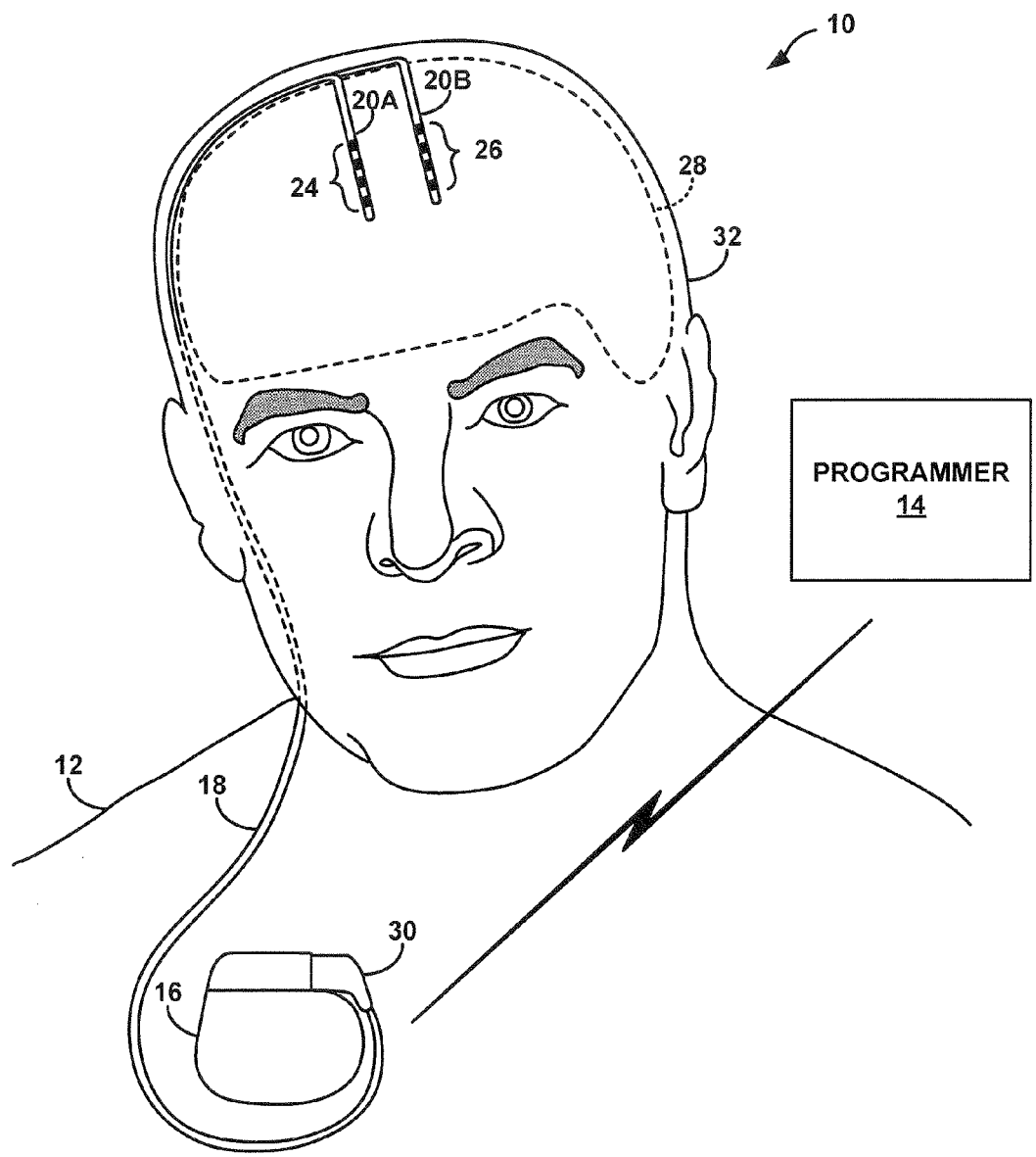
FIG. 9 is a conceptual diagram illustrating an example of a DBS system.

FIG. 9 is a conceptual diagram illustrating an example therapy system 10 that sensed brain signals and/or delivers therapy to manage a patient condition, such as a movement disorder, neurodegenerative impairment, a mood disorder or a seizure disorder of patient 12. Patient 12 ordinarily will be a human patient. In some cases, however, therapy system 10 may be applied to other mammalian or non-mammalian, non-human patients. While movement disorders and neurodegenerative impairment are primarily referred to herein, in other examples, therapy system 10 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post traumatic stress disorder, Parkinson's disease (PD), Alzheimer's Disease (AD), dysthymic disorder or obsessive-compulsive disorder (OCD)).

Therapy system 10 includes medical device programmer 14, implantable medical device (IMD) 16, lead extension 18, and leads 20A and 20B with respective sets of electrodes 24, 26. In the example shown in FIG. 9, electrodes 24, 26 of leads 20A, 20B (collectively referred to as "leads 20"), respectively, are positioned to deliver electrical stimulation to a tissue site within brain 28, such as a deep brain site under the dura mater of brain 28 of patient 12. In some examples, delivery of stimulation to one or more regions of brain 28, such as the subthalamic nucleus (e.g., the dorsal subthalamic nucleus), globus pallidus, internal capsule, thalamus or motor cortex, may be an effective treatment to mitigate or even eliminate one or more symptoms of various disorders, such as movement disorders.

Electrodes 24, 26 may also be positioned to sense bioelectrical signals within brain 28 of patient 12. In some examples, some of electrodes 24, 26 may be configured to only sense bioelectrical signals and other electrodes 24, 26 may be configured to only deliver electrical stimulation to brain 28. In other examples, some or all of electrodes 24, 26 are configured to both sense bioelectrical signals and deliver electrical stimulation to brain 28.

In various embodiments, IMD 16 includes a therapy module that includes a stimulation generator that generates and delivers electrical stimulation therapy to patient 12 via a subset of electrodes 24, 26 of leads 20A and 20B, respectively.

FIG. 9 illustrates use of an implantable medical device (IMD). Electrical stimulation generated by IMD 16 may be configured to manage a variety of disorders and conditions. In some examples, the stimulation generator of IMD 16 is configured to generate and deliver electrical pulses to patient 12 via electrodes of a selected stimulation electrode combination. However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may include a set of therapy parameter values, such as a stimulation electrode combination for delivering stimulation to patient 12, pulse frequency, pulse width, and a current or voltage amplitude of the pulses. The stimulation electrode combination may indicate the specific electrodes 24, 26 that are selected to deliver stimulation signals to tissue of patient 12 and the respective polarity of the selected electrodes. The pulse duty cycle, waveform, and pulse pattern may also be configured.

IMD 16 may be implanted within a subcutaneous pocket below the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing to substantially enclose components, such as a processor, therapy module, and memory. The devices, systems, and techniques described herein can be applied to a system that includes only one lead or more than two leads.

Although leads 20 are connected to IMD 16 via extension 18 in FIG. 9, leads 20 (or other lead(s)) may not be connected to an implanted device in some other implementations. For example, leads 20 can be connected to programmer 14 or other device having circuitry for processing bioelectrical signals for stereo data representation. A lead can be in the form of a probe having multiple electrodes along the length of the lead. The lead can be advanced within the brain during a procedure while data is collected. In some cases, collected data can be displayed during the procedure to facilitate navigation and/or understanding of how bioelectrical brain activity varies along the lead in real-time.

As shown in FIG. 9, implanted lead extension 18 is coupled to IMD 16 via connector 30 (also referred to as a connector block or a header of IMD 16). In the example of FIG. 9, lead extension 18 traverses from the implant site of IMD 16 and along the neck of patient 12 to cranium 32 of patient 12 to access brain 28. In the example shown in FIG. 1, leads 20A and 20B (collectively "leads 20") are implanted within the right and left hemispheres, respectively, of patient 12 in order to deliver electrical stimulation to one or more regions of brain 28, which may be selected based on the patient condition or disorder controlled by therapy system 10. The stimulation electrodes used to deliver stimulation to the target tissue site may be selected based on one or more sensed bioelectrical signals and a physiological model that indicates a region of brain 28 proximate the implanted electrodes, e.g., using the techniques described herein, e.g., with respect to FIGS. 1-9. Other lead 20 and IMD 16 implant sites are contemplated. For example, IMD 16 may be implanted on or within cranium 32, in some examples. As another example, leads 20 may be implanted within the same hemisphere of brain 28 or IMD 16 may be coupled to a single lead.

Although leads 20 are shown in FIG. 9 as being coupled to a common lead extension 18, in other examples, leads 20 may be coupled to IMD 16 via separate lead extensions or directly to connector 30. Leads 20 may be positioned to deliver electrical stimulation to one or more target tissue sites within and/or on brain 28 to manage patient symptoms associated with a patient condition, such as a movement disorder. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 or within the cerebral cortex of brain 28 via a burr hole in cranium 32 of patient 12, and electrically coupled to IMD 16 via one or more leads 20.

In the example shown in FIG. 9, electrodes 24, 26 of leads 20 are shown as ring electrodes. In other examples, electrodes 24, 26 may have different configurations. For example, in some examples, at least some of the electrodes 24, 26 of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed in a specific direction from leads 20 to enhance therapy efficacy and reduce possible adverse side effects from stimulating a large volume of tissue. An example of a complex electrode array geometry including segmented electrodes is shown and described with reference to FIGS. 3A and 3B. In some examples, a housing of IMD 16 may include one or more stimulation and/or sensing electrodes. In alternative examples, leads 20 may have shapes other than elongated cylinders as shown in FIG. 9. For example, leads 20 may be paddle leads, spherical leads, bendable leads, or any other type of shape effective in treating patient 12 and/or minimizing invasiveness of leads 20. In addition, in other examples, leads 20 may include both macro electrodes (e.g., rings, segments adapted to sensing local field potentials and stimulation) and micro electrodes (e.g., adapted to sensing spike trains in the time domain) in any combination.

Figure 10:
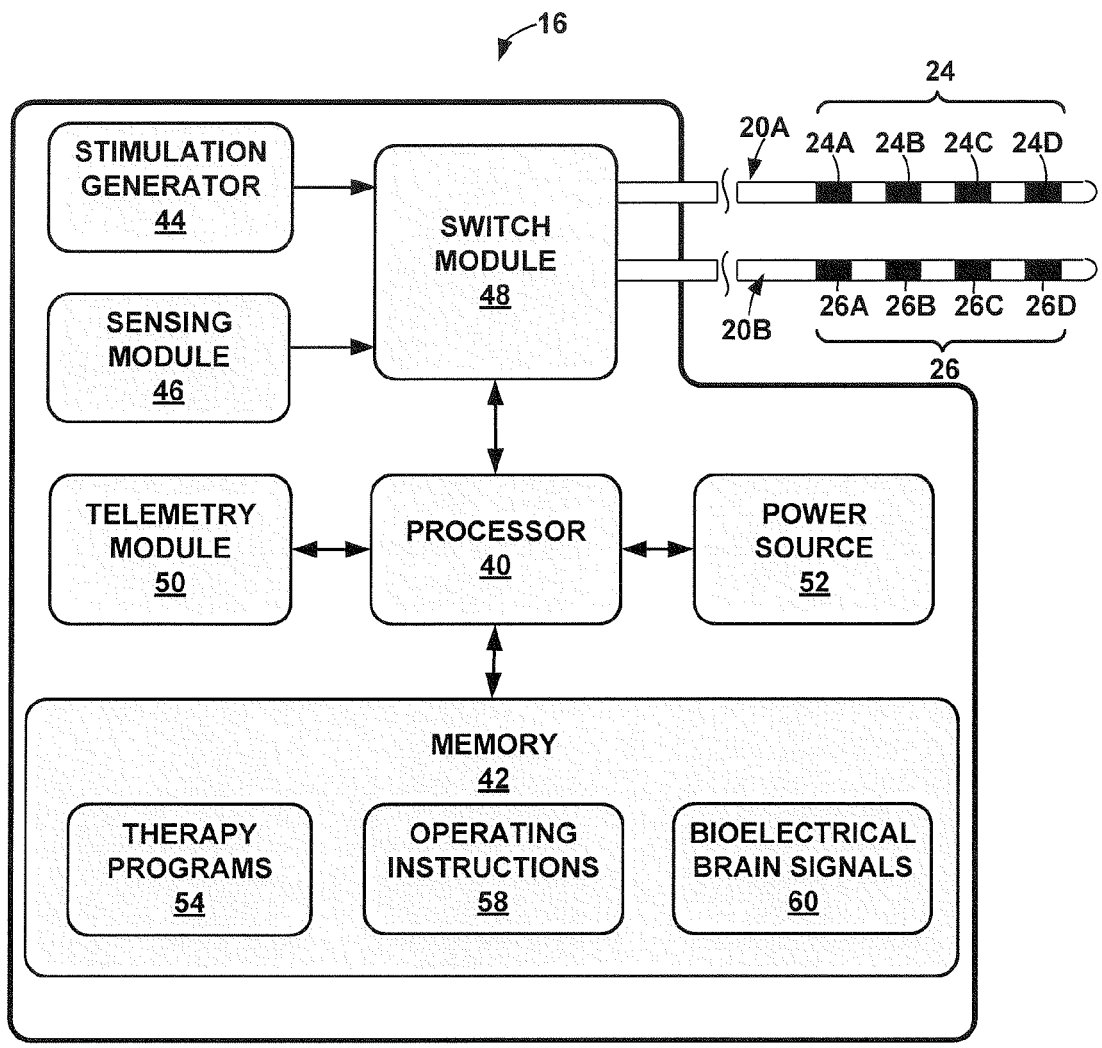
FIG. 10 is functional block diagram illustrating components of an example medical device.

FIG. 10 is a functional block diagram illustrating components of an example IMD 16. In the example shown in FIG. 10, IMD 16 includes processor 40, memory 42, stimulation generator 44, sensing module 46, switch module 48, telemetry module 50, and power source 52, which can be control circuitry as means for performing functions as described herein. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 is a physical structure that may store computer-readable instructions that, when executed by processor 40, cause IMD 16 to perform various functions.

In the example shown in FIG. 10, memory 42 stores therapy programs 54, bioelectrical signals 60, and operating instructions 58 in separate memories within memory 42 or separate areas within memory 42. Each stored therapy program 54 defines a particular set of electrical stimulation parameters, such as a stimulation electrode combination, current or voltage amplitude, frequency (e.g., pulse rate in the case of stimulation pulses), and pulse width.

Bioelectrical signals 60 include bioelectrical signals sensed within brain 28 of patient 12 by sensing module 46. Example bioelectrical signals include, but are not limited to, a signal generated from local field potentials within one or more regions of brain 28. EEG and ECoG signals are examples of signals that may be measured from brain 28. However, local field potentials may include a broader genus of electrical signals within brain 28 of patient 12. In some examples, bioelectrical signals 60 are raw bioelectrical signals sensed by sensing module 46 (or another sensing module), a parameterized bioelectrical signal generated by sensing module 46 or data generated based on the raw bioelectrical signal. Operating instructions 58 guide general operation of IMD 16 under control of processor 40.

Stimulation generator 44, under the control of processor 40, generates stimulation signals for delivery to patient 12 via a selected subset of electrodes 24, 26.

Processor 40 may include any one or more of a microprocessor, a controller, a digital signal processor (DSP), an application specific integrated circuit (ASIC), a field-programmable gate array (FPGA), microcontroller, or discrete logic circuitry. The functions attributed to processors described herein may be embodied in a hardware device via software, firmware, hardware or any combination thereof. Processor 40 controls sensing and processing of signals and stimulation generator 44 according to therapy programs 54 stored in memory 42 to apply particular stimulation parameter values specified by one or more of programs, such as amplitude, pulse width, and pulse rate.

In the example shown in FIG. 10, the set of electrodes 24 includes electrodes 24A, 24B, 24C, and 24D, and the set of electrodes 26 includes electrodes 26A, 26B, 26C, and 26D. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical signals with selected electrodes 24, 26. Hence, stimulation generator 44 is coupled to electrodes 24, 26 via switch module 48 and conductors within leads 20. In some examples, however, IMD 16 does not include switch module 48.

Stimulation generator 44 can be a single channel or multi-channel stimulation generator. In particular, stimulation generator 44 may be capable of delivering a single stimulation pulse, multiple stimulation pulses, or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

In some examples, processor 40 dynamically changes the selected combinations of electrodes 24, 26, i.e., the stimulation electrode combination, based on one or more frequency domain characteristics of bioelectrical signals sensed within brain 28. Sensing module 46, under the control of processor 40, may sense bioelectrical signals and provide the sensed bioelectrical signals to processor 40. Processor 40 may control switch module 48 to couple sensing module 46 to a selected combination of electrodes 24, 26, e.g., a sense electrode combination. In this way, IMD 16 may be configured such that sensing module 46 may sense bioelectrical signals with a plurality of different sense electrode combinations. Switch module 48 may be electrically coupled to the selected electrodes 24, 26 via the conductors within the respective leads 20, which, in turn, deliver the bioelectrical signal sensed across the selected electrodes 24, 26 to sensing module 46. The bioelectrical signal may include electrical signals that are indicative of electrical activity within brain 28 of patient 12. Processor 40 can store the sensed bioelectrical signals in memory 42.

Although sensing module 46 is incorporated into a common housing with stimulation generator 44 and processor 40 in FIG. 10, in other examples, sensing module 46 may be in a separate housing from IMD 16 and may communicate with processor 40 (and, in some examples, programmer 14) via wired or wireless communication techniques.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by RF communication techniques. In addition, telemetry module 50 may communicate with external medical device programmer 114 via proximal inductive interaction of IMD 16 with programmer 14. Accordingly, telemetry module 50 may send information, such as information relating to sensed bioelectrical signals, including bioelectrical signals themselves, to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16.

Figure 11:
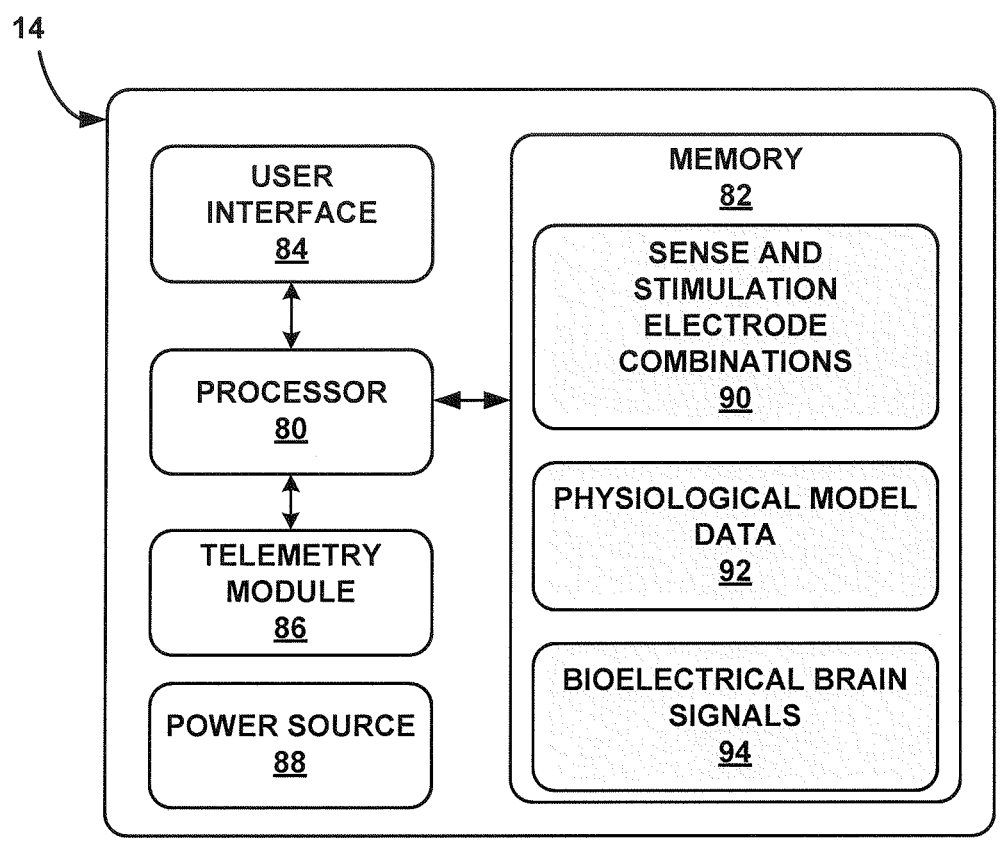
FIG. 11 is a functional block diagram illustrating components of an example medical device programmer.

FIG. 11 illustrates an external programmer 14 that can embody various aspects of the present disclosure. External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16.

Alternatively, programmer 14 may be a patient programmer that allows patient 12 to select programs and/or view and modify therapy parameters.

Programmer 14 may be a hand-held computing device with a display viewable by the user and an interface for providing input to programmer 14 (i.e., a user input mechanism). For example, programmer 14 may include a display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., activation of power, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as medical device programmer 14. A wireless adapter coupled to the computing device may enable secure communication between the computing device and IMD 16. The circuitry of programmer 14 and/or other external device(s) can be control circuitry as means for performing functions as described herein.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20 or delivering electrical stimulation within brain to measure evoked responses).

Programmer 14 is configured to communicate to 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the IEEE 802.11 or Bluetooth® specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

FIG. 11 is a conceptual block diagram of an example external medical device programmer 14, which includes processor 80, memory 82, user interface 84, telemetry module 86, and power source 88. Processor 80 controls user interface 84 and telemetry module 86, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 84. User interface 84 includes a display (not shown), such as an LCD or LED display or other type of screen, to present information related to the therapy, such as information related to bioelectrical signals sensed via, a plurality of sense electrode combinations. In addition, user interface 84 may include an input mechanism to receive input from the user. The input mechanisms may include, for example, buttons, a keypad (e.g., an alphanumeric keypad), a peripheral pointing device, or another input mechanism that allows the user to navigate though user interfaces presented by processor 80 of programmer 14 and provide input.

In some examples, at least some of the control of therapy delivery by IMD 16 may be implemented by processor 80 of programmer 14. In addition, in some examples, processor 80 may select a stimulation electrode combination based on a bioelectrical signal sensed by IMD 16 and a physiological model that indicates a one or more characteristics of tissue of brain 28 of patient 12 proximate implanted electrodes 24, 26 of leads 20. The examples described herein primarily refer to a bioelectrical signal sensed by IMD 16, but are also applicable to selecting an electrode combination based on a bioelectrical signal sensed by a sensing module that is separate from IMD 16. The separate sensing module may, but need not be, implanted within patient 12.

In the example shown in FIG. 11, memory 82 stores sense and stimulation electrode combinations 90, physiological model data 92, and bioelectrical signals 94 in separate memories within memory 82 or separate areas within memory 82. Memory 82 may also include instructions for operating user interface 84 and telemetry module 86, and for managing power source 88. Memory 82 may also store any therapy data retrieved from IMD 16 during the course of therapy, such as bioelectrical signals 94 sensed by IMD 16. The clinician may use this therapy data to determine the progression of the patient condition in order to predict future treatment. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient Wireless telemetry in programmer 14 may be accomplished by RF communication or proximal inductive interaction of external programmer 14 with IMD 16. This wireless communication is possible through the use of telemetry module 86. Accordingly, telemetry module 86 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 88 delivers operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet, in addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

In various embodiments, a lead is not connected to an during sensing of bioelectrical signals but rather is connected to a programmer or other external circuitry by a cable having conductors for conducting the signals to the programmer or other external circuitry. Such a lead can then be used as a probe and advanced into the brain. Based on sensed bioelectrical signals, parameters of signal data sets may be displayed as data representations on a screen using the techniques and features discussed herein. As such, a programmer or other external circuitry may have the equivalent circuitry of FIG. 10, including sensing module 46 for amplifying and measuring the bioelectrical signals. The lead may be temporarily placed in the brain for sensing of data for stereo data representation. In some embodiments, the lead may be disconnected form the external device and connected to an IMD for chronic implantation.

In some embodiments, a data representation along a lead may indicate the presence or strength of a biomarker sensed via an electrode or electrode combination. A processor may determine whether the bioelectrical signal includes a biomarker. A biomarker may be, for example, indicative of a target tissue site or target tissue (e.g., a brain portion targeted for sensing and/or therapy). The biomarker can be, for example, a signal characteristic, such as the mean, median, peak or lowest amplitude of the section of the bioelectrical signal, a match to a template, or a frequency domain characteristic of the sensed bioelectrical signal (e.g., the power level within a particular frequency band or a ratio of power levels within two frequency bands). Other biomarkers are also contemplated for being represented along electrodes and a lead consistent with this disclosure. Different regions of a brain may exhibit different potentials, such that bioelectrical signals sensed with electrodes in the different regions of a brain can result in bioelectrical signals having different signal characteristics. These different signal characteristics can be biomarkers for a target tissue site. In this way, the signal characteristics of a bioelectrical signal can be used to determine whether the electrodes of the selected electrode combination are proximate the target tissue site or the tissue site associated with the stimulation-induced side effect using stereo data representation as discussed herein. For example, a parameter of a biomarker (e.g., amplitude of signal or dominant frequency component) can be displayed for multiple data representations along the length of a lead in spatial association with respective sensing electrodes. Memory 82 of programmer 14 or a memory of another device can store signal characteristics. In some examples, processor 80 compares a characteristic of the sensed bioelectrical signal with a predetermined threshold value or template stored by memory 82 of programmer 14 or a memory of another device. The predetermined threshold value or template stored by memory 82 of programmer 14 can be selected by a clinician or processor 80 to represent a biomarker, e.g., characteristic of a signal that is sensed within the target tissue site within brain 28.

A biomarker may be a time domain characteristics of a sensed bioelectrical signal, such as a sensed spike train from an individual or small group of neurons. Such spikes may be identified by a processor by amplitude of a frequency domain characteristic of a bioelectrical signal. In this way, a biomarker may be identified from a signal and represented on a display along the electrode that sensed the signal. As such, identifying frequency domain characteristics of the sensed bioelectrical signals may be performed by a processor implementing an algorithm. Biomarkers may also be identified by a mean, median, peak or lowest amplitude greater or less than a predetermined threshold value of a bioelectrical signal.

A bioelectrical signal having a pattern (e.g., a time domain pattern) substantially correlating (e.g., a 100% match may not be required, but may be within a threshold percentage, such as about a 75% to about a 100% match) to a template stored in memory may be used to identify a biomarker. A biomarker may be identified by a particular number of spikes within a particular time frame. A frequency domain characteristic of a bioelectrical signal may include, for example, a power level (or energy) within one or more frequency bands of the bioelectrical signal, a ratio of the power level in two or more frequency bands, a correlation in change of power between two or more frequency bands, a pattern in the power level of one or more frequency bands over time, and the like, any of which can be used to identify a biomarker that is represented as data on a display in spatial association with the respective electrode or electrode combination used to sense the bioelectrical signal.

For a particular patient condition, one or more specific frequency bands may be more revealing of a useful biomarker for representation on a display. Processor 40 of IMD 16, processor 80 of programmer 14 or a processor of another device may perform a spectral analysis of the bioelectrical signal in the revealing frequency bands. The spectral analysis of a bioelectrical signal may indicate the power level of each bioelectrical signal within each given frequency band over a range of frequencies. While the beta frequency band is primarily referred to herein, in other examples, processor 40 or processor 80 may select a stimulation electrode combination based on the power level within one or more frequency bands other than the beta band.

For example, processor 40 or processor 80 may compare the power levels of a frequency band other than the beta band in bioelectrical signals sensed by different electrodes to determine relative values of the power levels for combinations of electrodes. Processor 40 or processor 80 may then determine which of the electrodes is closest to a target tissue site based on the relative values. Rankings for the relative distances of the electrodes or other parameters indicating the relative distance of the electrodes can then be displayed as parameters of data representations.

Different frequency bands are associated with different activity in brain 28. It is believed that some frequency band components of a bioelectrical signal from within brain 28 may be more revealing of particular patient condition and abnormal brain activity associated with the particular patient condition than other frequency components. One example of the frequency bands is shown in Table 1:

TABLE 1

| Frequency (f) Band Hertz (Hz) | Frequency Information |
|---|---|
| f < 4 Hz | δ (delta frequency band) |
| 4 Hz ≤ f ≤ 8 Hz | theta frequency band |
| 8 Hz ≤ f ≤ 13 Hz | α (alpha frequency band) |
| 13 Hz ≤ f ≤ 35 Hz | β (beta frequency band) |
| 35 Hz ≤ f ≤ 100 Hz | γ (gamma frequency band) |
| 100 Hz ≤ f ≤ 200 Hz | high γ (high gamma frequency band) |

The frequency ranges for the frequency bands shown in Table 1 are merely examples. The frequency ranges may differ in other examples.

In one example, a clinician may select the frequency band of a bioelectrical signal for identifying biomarkers based on information specific to a patient or based on data gathered from more than one patient. Such biomarker can then be identified from sensed signals and a data representation can be displayed alongside an associated electrode or electrode combination to indicate that strength of the electrode(s) in sensing the frequency band. Further discussing frequency bands, the entire content of U.S. patent application Ser. Nos. 12/639,717 and 12/639,678 are hereby incorporated by reference.

The methods and systems referenced herein can be employed for a variety of purposes, including selection electrodes or electrode combinations for sensing and/or therapy delivery, which is further described in patent application STIMULATION ELECTRODE SELECTION by Molnar et al., U.S. patent application Ser. No. 12/768,403, filed on Apr. 27, 2010, which is incorporated herein by reference in its entirety.

It is noted that a lead may be in the form of a probe. In this way, probe and its contacts can be used as surrogates for a lead. The devices, systems, and techniques described with respect to FIGS. 1-11 can also be used with electrically active areas of a probe or other member. Such a probe can be, for example, an apparatus that includes electrical contacts in a similar configuration as the one or more leads that the clinician anticipates implanting within a brain. A clinician may position the probe within a brain of a patient in order to locate the target tissue site or locate a tissue site related to stimulation-induced side effects.

The techniques described in this disclosure, including those attributed to a programmer, IMD, display system, control circuitry, or various constituent components, may be implemented, at least in part, in hardware, software, firmware or any combination thereof. For example, various aspects of the techniques may be implemented within one or more processors, including one or more microprocessors, DSPs, ASICs, FPGAs, microcontroller, or any other equivalent integrated or discrete logic circuitry, as well as any combinations of such components, embodied in programmers, such as physician or patient programmers, stimulators, image processing devices or other devices. The term "control circuitry" generally refers to at least one of the foregoing logic circuitry as a processor, alone or in combination with other logic circuitry, or any other equivalent circuitry. The circuitry of control circuitry may therefore be distributed between multiple separate devices, and may be duplicated between the different devices. For example, control circuitry may refer to any of the components of FIGS. 10-11, and/or other FIG. presented herein, working alone or together to carry out any of the functions for which the control circuitry is configured. Furthermore, control circuitry may refer to memory having program instructions executable by a processor of the control circuitry for carrying out the functions as described herein.

Such hardware, software, firmware may be implemented within the same device or within separate devices to support the various operations and functions described in this disclosure. While the techniques described herein are primarily described as being performed by a programmer, any one or more parts of the techniques described herein may be implemented by a processor of one of IMD 16, programmer 14, or another computing device, alone or in combination with each other.

Although programmers may have been illustrated in different figures and indicated by different reference numbers, it is intended that any functionally described in connection with any one programmer can be used in any other programmer. For example, programmers 260, 360, 460, 560, 660, and 14 can be the same programmer or represent common functionality. Likewise, the data representation and other display schemes of the various figures can be used together.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. In this way, the present disclosure is presented in an exemplary, non-limiting format, and is not intended to present the limited ways in which the various aspects of the present disclosure can be implemented.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Figure 12:
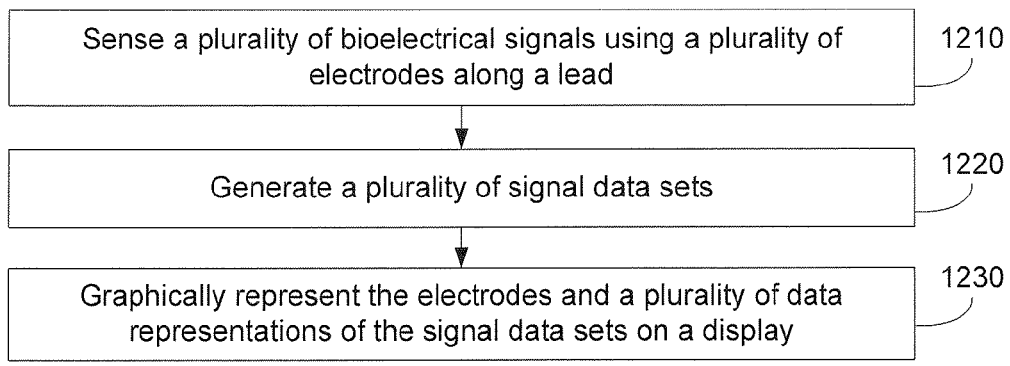
FIGS. 12 and 13 are flow charts for implementing stereo data representation along a lead.

FIG. 12 illustrates a method 1200 for stereo data representation along a sensing lead, the steps of which may be implemented by control circuitry of a medical device configured (e.g., with program instructions stored in memory) to carry out the steps. The method 1200 includes sensing 1210 a plurality of bioelectrical signals using a plurality of electrodes along a lead. The electrodes of the plurality have a spatial configuration along the lead, such as in a 1×3×3×1 arrangement as in FIG. 3. The method 1200 further includes generating 1220 a plurality of signal data sets. In various cases, one signal data set is generated 1220 for each bioelectrical signal of the plurality of bioelectrical signals.

The method 1200 further includes graphically representing 1230 the electrodes and a plurality of data representations of the signal data sets on a display. The display may be, for example, the display of a programmer. In various embodiments, each data representation of the plurality indicates a parameter of a respective one of the plurality of data sets (e.g., a parameter indicative of the relative presence of a biomarker). In some cases, the electrodes are graphically represented 1230 on the display in a spatial configuration representative of the spatial configuration of the plurality of electrodes along the lead and each data representation is graphically represented 1230 on the display in spatial association with at least one electrode through which the bioelectrical signal on which the signal data set is based was sensed 1210. Each data representation may comprise, for example, a line between two of the electrode representations from which the bioelectrical signal on which the data representation is based was sensed 1210. In some cases, each data representation comprises at least one parameter of stimulation output.

In various embodiments, generating 1220 the plurality of signal data sets comprises determining the relative presence of a biomarker in each of the plurality of bioelectrical signals. The biomarker may comprises one or both of beta band power content and gamma band power content. In various embodiments, each of the plurality of bioelectrical signals is sensed 1210 using a different electrode combination of the plurality of electrodes and each data representation is graphically represented 1230 on the display in spatial association with the electrode combination with which the bioelectrical signal on which the parameter of the data representation is based was sensed 1210. Each data representation of each signal data set may be graphically represented 1230 on the display in proximate spatial association with the electrode or electrode combination on which the signal data set is based such that the closest data representation on the display to any electrode or electrode combination is the data representation that is based on the bioelectrical signal sensed 1210 using the electrode or electrode combination.

The method 1200 may include comparing the data sets of the plurality of data sets to each other, wherein graphically representing 1230 the data representations comprises only displaying a number of data representations of those data sets (i.e. such that not all data sets are represented by a data representation) that are associated with greater sensing of a particular signal component relative to others of the signal data sets based on the comparison, wherein the number is at least two.

Figure 13:
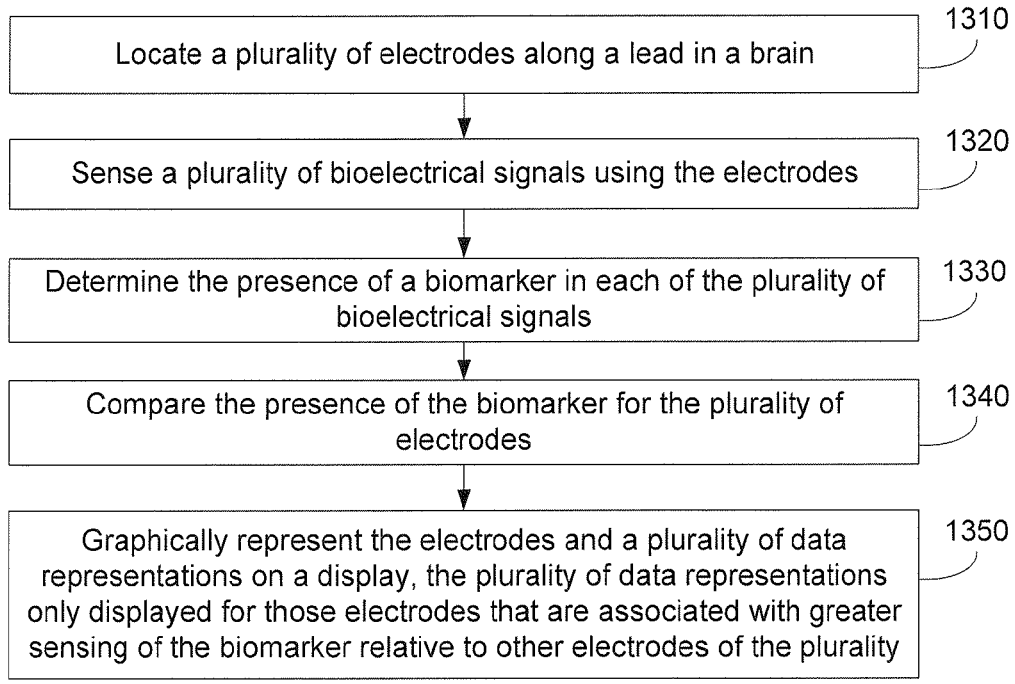

FIG. 13 illustrates a method 1300 for stereo data representation along a sensing lead, for which most of the steps may be implemented by control circuitry of a medical device configured (e.g., with program instructions stored in memory) to carry out the steps. It is noted that the method 1300 of FIG. 13 may be the same method 1200 of FIG. 12, with the respective flow charts highlighting different aspects of stereo data representation. The method 1300 includes locating 1310 a plurality of electrodes along a lead in a brain, the plurality of electrodes having a spatial configuration along the lead. While locating 1310 the electrodes in the brain is used as an example in this case, other anatomical areas are contemplated, such as along a surface of a brain or proximate another organ. A plurality of bioelectrical signals can be sensed 1320 using the electrodes. Based on the sensed 1320 signals, the presence of a biomarker in each of the plurality of bioelectrical signals can be determined 1330. The determined 1330 presence may be the absolute measured presence of the biomarker in a signal. The biomarker may be any parameter referenced herein, such as one or both of beta band power content and gamma band power content in the signals. The determined 1330 presence of the biomarker for each bioelectrical signal can then be compared 1340 for each signal. Such comparison 1340 can determine which signal has the most of a particular type of signal content, for example, and can rank the signals on the basis of the amount of the content in each signal (e.g., those signals with the most of a particular type of content are ranked highest while those signals with the least of the particular type of content are ranked lowest).

The method 1300 further includes graphically representing 1350 the electrodes and a plurality of data representations on a display, the plurality of data representations only displayed for those electrodes that are associated with greater sensing of the biomarker relative to other electrodes of the plurality. In some embodiments, only the top three or top five electrodes or electrode combinations associated with the highest particular type of signal content will have a data representation displayed in spatial association with the electrodes. The determination of which electrodes will have associated data representations displayed is based on the comparison 1340, such as by only displaying those data representations for electrodes or electrode combinations associated with higher ranked signals. In various embodiments, each data representation of the plurality indicates a parameter of a respective one of the signals, the electrodes are graphically represented 1350 on the display in a spatial configuration representative of the spatial configuration of the plurality of electrodes along the lead, and each data representation is graphically represented 1350 on the display in spatial association with at least one electrode through which the bioelectrical signal on which the data representation is based was sensed 1320.

The various techniques, features, and components discussed herein in various embodiments are applicable to various other embodiments in different configurations and combinations, as the present disclosure makes use of examples to illustrate options which are not limited to the specific embodiments presented. As such, each example embodiment should be understood to be combinable and modifiable in view of the other embodiments presented herein. Various examples of the invention have been described. These and other examples are within the scope of the following claims.

We claim:

1. A method of stereo data representation along a sensing lead, the method comprising:
    sensing a plurality of bioelectrical signals using a plurality of electrodes along a lead, the plurality of electrodes having a spatial configuration along the lead;
    generating a plurality of signal data sets, one signal data set being generated for each bioelectrical signal of the plurality of bioelectrical signals; and
    graphically representing the electrodes and a plurality of data representations of the signal data sets on a display, wherein each data representation of the plurality indicates a parameter of a respective one of the plurality of data sets, wherein the electrodes are graphically represented on the display in a spatial configuration representative of the spatial configuration of the plurality of electrodes along the lead, wherein each data representation is graphically represented on the display in spatial association with at least one electrode of an electrode combination through which the bioelectrical signal on which the signal data set is based was sensed, wherein each data representation comprises an electrode combination indicator that identifies the electrode combination through which the bioelectrical signal on which the data representation is based was sensed, and wherein generating and graphically representing are each performed at least in part by medical device control circuitry.

2. The method of claim 1, wherein generating the plurality of signal data sets comprises determining the relative presence of a biomarker in each of the plurality of bioelectrical signals and wherein the parameter is indicative of the relative presence of the biomarker.

3. The method of claim 2, wherein the biomarker comprises one or both of beta band power content and gamma band power content.

4. The method of claim 2, wherein the data representations indicate the parameter by one or more of color, value, or line pattern, and wherein the color, value, or line pattern is variable based on the relative presence of the biomarker.

5. The method of claim 1, wherein:
each of the plurality of bioelectrical signals is sensed using a different electrode combination of the plurality of electrodes; and
each data representation is graphically represented on the display in spatial association with the electrode combination through which the bioelectrical signal on which the parameter of the data representation is based was sensed.

6. The method of claim 1, wherein:
generating the plurality of signal data sets comprises generating a plurality of traces, each trace of the plurality generated from a respective one of the plurality of bioelectrical signals; and
graphically representing the data representations comprises graphically representing the traces.

7. The method of claim 1, wherein each electrode combination indicator comprises a line between two of the electrode representations from which the bioelectrical signal on which the data representation is based was sensed.

8. The method of claim 1, wherein each data representation comprises at least one parameter of stimulation output.

9. The method of claim 1, further comprising comparing the data sets of the plurality of data sets to each other, wherein graphically representing the data representations comprises only displaying a number of data representations of those data sets that are associated with greater sensing of a particular signal component relative to others of the signal data sets based on the comparison, wherein the number is at least two.

10. The method of claim 1, furthering comprising determining a spatial positioning of the lead in a human brain, wherein graphically representing the electrodes and the data representations on the display further comprises graphically representing an anatomical brain model on the display and graphically representing the electrodes in spatial association with the anatomical brain model representing the spatial positioning of the lead in the human brain.

11. The method of claim 1, wherein each data representation of each signal data set is graphically represented on the display in proximate spatial association with the electrode on which the signal data set is based such that the closest data representation on the display to any electrode is the data representation that is based on the bioelectrical signal sensed using the electrode.

12. The method of claim 1, wherein each data representation is graphically represented on the display in proximate spatial association with the electrode combination on which a associated signal data set is based such that the closest data representation on the display to any electrode combination is the data representation that is based on the bioelectrical signal sensed using the electrode combination.

13. The method of claim 1, wherein the lead is configured to be coupled with an implantable medical device.

14. A system comprising:
a lead having a plurality of electrodes, the plurality of electrodes having a spatial configuration along the lead;
a display; and
control circuitry, the control circuitry configured to:
sense a plurality of bioelectrical signals using the plurality of electrodes;
generate a plurality of signal data sets, one signal data set being generated for each bioelectrical signal of the plurality of bioelectrical signals; and
graphically represent the electrodes and a plurality of data representations of the signal data sets on the display, wherein the control circuitry is configured to graphically represent the electrodes and the plurality of data representations such that each data representation of the plurality indicates a parameter of a respective one of the plurality of data sets, the electrodes are graphically represented on the display in a spatial configuration representative of the spatial configuration of the plurality of electrodes of the lead, and each data representation is graphically represented on the display in spatial association with at least one electrode of an electrode combination through which the bioelectrical signal on which the signal data set is based was sensed, and wherein each data representation comprises an electrode combination indicator which identifies the electrode combination through which the bioelectrical signal on which the data representation is based was sensed.

15. The system of claim 14, wherein generation of the signal data sets by the control circuitry comprises determining the relative presence of a biomarker in each of the plurality of bioelectrical signals, and wherein the parameter is indicative of the relative presence of the biomarker.

16. The system of claim 15, wherein the biomarker comprises one or both of beta band power content and gamma band power content.

17. The system of claim 15, wherein the parameter is indicated for each data representation by one or more of color, value, and line pattern, and wherein the color, value, and line pattern are each variable based on the relative presence of the biomarker.

18. The system of claim 14, wherein the control circuitry is configured to:
sense each of the plurality of bioelectrical signals using a different electrode combination of the plurality of electrodes;
graphically represent each data representation on the display in spatial association with the electrode combination with which the bioelectrical signal on which the parameter of the data representation is based was sensed.

19. The system of claim 14, wherein the control circuitry is configured to:
generate a plurality of traces as a part of generating the plurality of signal data sets, each trace of the plurality generated from a respective one of the plurality of bioelectrical signals; and
graphically represent the traces as part of graphically representing the data representations.

20. The system of claim 14, wherein each electrode combination indicator comprises a line between two of the electrode representations from which the bioelectrical signal on which the data representation is based was sensed.

21. The system of claim 14, wherein:
the control circuitry is further configured to deliver electrical stimulation from the plurality of electrodes;
the control circuitry is further configured to sense the plurality of bioelectrical signals timed to collect include invoked response data; and
each data representation indicates a first parameter of a stimulation output parameter and a second parameter indicative of the invoked response data.

22. The system of claim 14, wherein the control circuitry is further configured to:
compare the data sets of the plurality of data sets to each other; and
graphically represent the data representations such that only a number of data representations of those data sets that are associated with greater sensing of a particular signal component relative to others of the signal data sets based on the comparison are displayed, wherein the number is at least two.

23. The system of claim 14, wherein the control circuitry is further configured to:
determine a spatial positioning of the lead in a human brain; and
graphically represent an anatomical brain model on the display and graphically represent the electrodes in spatial association with the anatomical brain model representing the spatial positioning of the lead in the human brain.

24. The system of claim 14, wherein the control circuitry is configured to graphically represent each data representation of each signal data set on the display in proximate spatial association with the electrode on which the signal data set is based such that the closest data representation on the display to any electrode is the data representation that is based on the bioelectrical signal sensed using the electrode.

25. The system of claim 14, wherein the control circuitry is configured to graphically represent each data representation on the display in proximate spatial association with the electrode combination on which an associated signal data set is based such that the closest data representation on the display to any electrode combination is the data representation that is based on the bioelectrical signal sensed using the electrode combination.

26. The system of claim 14, wherein the lead is configured to be coupled with an implantable medical device.

27. A system comprising:
means for sensing a plurality of bioelectrical signals using a plurality of electrodes along a lead, the plurality of electrodes having a spatial configuration along the lead;
means for generating a plurality of signal data sets, one signal data set being generated for each bioelectrical signal of the plurality of bioelectrical signals; and
means for graphically representing the electrodes and a plurality of data representations of the signal data sets on a display, wherein each data representation of the plurality indicates a parameter of a respective one of the plurality of data sets, wherein the electrodes are graphically represented on the display in a spatial configuration representative of the spatial configuration of the plurality of electrodes along the lead, wherein each data representation is graphically represented on the display in spatial association with at least one electrode of an electrode combination through which the bioelectrical signal on which the signal data set is based was sensed, wherein each data representation comprises an electrode combination indicator which identifies the electrode combination through which the bioelectrical signal on which the data representation is based was sensed, and wherein generating and graphically representing are each performed at least in part by a processor.

28. The system of claim 27, wherein the means for generating the plurality of signal data sets comprises means for determining the relative presence of a biomarker in each of the plurality of bioelectrical signals and wherein the parameter is indicative of the relative presence of the biomarker.

29. A computer readable medium comprising instructions for causing a medical device to perform steps comprising:
sensing a plurality of bioelectrical signals using a plurality of electrodes along a lead, the plurality of electrodes having a spatial configuration along the lead;
generating a plurality of signal data sets at least in part by determining the relative presence of a biomarker in each of the plurality of bioelectrical signals, one signal data set being generated for each bioelectrical signal of the plurality of bioelectrical signals; and
graphically representing the electrodes and a plurality of data representations of the signal data sets on a display, wherein each data representation of the plurality indicates a parameter of a respective one of the plurality of data sets and the parameter is indicative of the relative presence of the biomarker, wherein the electrodes are graphically represented on the display in a spatial configuration representative of the spatial configuration of the plurality of electrodes along the lead, and wherein each data representation is graphically represented on the display in spatial association with at least one electrode of an electrode combination through which the bioelectrical signal on which the signal data set is based was sensed, wherein each data representation comprises an electrode combination indicator which identifies the electrode combination through which the bioelectrical signal on which the data representation is based was sensed, and wherein generating and graphically representing are each performed at least in part by a processor.

* * * * *